(12) United States Patent
Soga et al.

(10) Patent No.: US 6,677,456 B2
(45) Date of Patent: Jan. 13, 2004

(54) PENTACYCLIC TAXAN COMPOUND

(75) Inventors: Tsunehiko Soga, Edogawa-ku (JP);
Kouichi Uoto, Edogawa-ku (JP);
Yasuyuki Takeda, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 17 days.

(21) Appl. No.: 10/091,023

(22) Filed: Mar. 6, 2002

(65) Prior Publication Data

US 2002/0143178 A1 Oct. 3, 2002

Related U.S. Application Data

(63) Continuation-in-part of application No. PCT/JP00/07087, filed on Oct. 12, 2000.

(30) Foreign Application Priority Data

Oct. 15, 1999 (JP) .......................................... P 11-293356
Mar. 7, 2001 (JP) ..................................... P 2001-063841

(51) Int. Cl.⁷ .................... C07D 405/08; C07D 305/14; A61K 31/337; A61K 31/44
(52) U.S. Cl. .................... 546/284.1; 514/338; 514/449; 514/463; 549/440; 549/441; 549/444; 549/446; 549/510; 549/511
(58) Field of Search ................................ 549/510, 511, 549/446, 444, 441, 440; 514/463, 449, 338; 546/284.1

(56) References Cited

FOREIGN PATENT DOCUMENTS

| | | |
|---|---|---|
| EP | 0 826 688 A1 | 3/1998 |
| WO | WO 95/13270 A | 5/1995 |
| WO | WO 97/46260 A | 12/1997 |

OTHER PUBLICATIONS

International Search Report.

H. Poujol, et al, Taxoides: 7–Deshydroxy–10–acetyldocetaxel et Nouveaux Analogues Prepares a partir des Alcaloides de l'If', Tetrahedon, vol. 53, No. 37, 1997, pp. 12575–12594, XP002236565.

*Primary Examiner*—Ba K. Trinh
(74) *Attorney, Agent, or Firm*—Sughrue Mion, PLLC

(57) ABSTRACT

This invention is to provide a novel taxol derivative useful as an antitumor compound having respective substituent groups, represented by the following formula (I) which can be orally administered

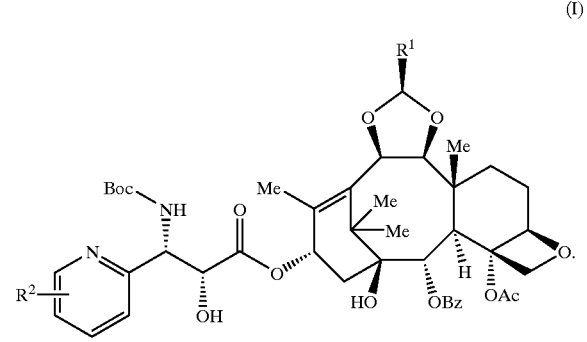

20 Claims, 1 Drawing Sheet

PENTACYCLIC TAXAN COMPOUND

This is a Continuation-In-Part of International Application PCT/JP00/07087, with an international filing date of Oct. 12, 2000, which was published under PCT Article 21(2), and the complete disclosure of which is incorporated into this application by reference.

TECHNICAL FIELD

This invention relates to a taxol derivative which can be administered orally and has an antitumor activity.

BACKGROUND ART

Taxol is a natural substance represented by the following chemical structural formula, which can be obtained in a small amount from a bark or other parts of *Taxus brevifolia*.

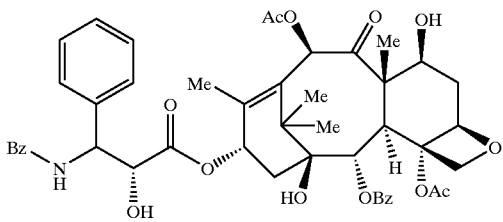

It is known that taxol has an antitumor activity, and its action mechanism is considered to be based on its action to inhibit depolymerization of microtubules in cell division, so that its clinical application is expected as an antitumor agent having an action mechanism which is different from the conventional antitumor agents.

Taxol has so far been obtained from a natural source but only in an extremely small amount. However, taxol derivatives synthesized using a taxol precursor 10-O-deacetylbaccatine III represented by the following formula, which can be obtained from leaves and other parts of Taxus plants in a relatively large amount, have been reported.

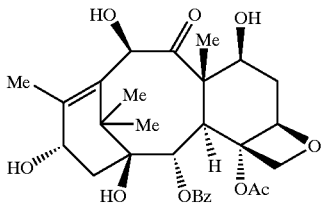

Among them, a compound (taxotere, hereinafter referred to as "compound A") having a structure of the following formula (A) has been drawing attention as a compound having an antitumor activity equal to or higher than that of taxol, and its development as an antitumor agent is in progress.

(A)

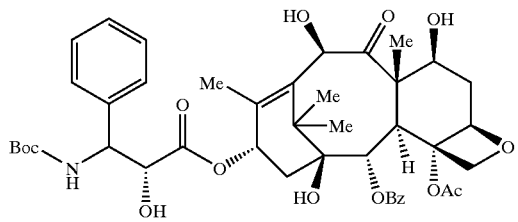

The present inventors have reported that a compound obtained by converting a hydroxyl group formed by reduction of the 9-position ketone and a hydroxyl group of the 10-position into a cyclic acetal form has a strong antitumor activity (JP-A-9-12578 (the term "JP-A" as used herein refers to a "published unexamined Japanese patent application") and EP 0 826 688 A1.

Taxol, taxotere and the compound disclosed in JP-A-9-12578 are promising as antitumor agents. However, efficacy of these compounds by oral administration is not known. Regarding the compounds disclosed in Examples of JP-A-9-12578, it has a drawback from the toxicity point of view. From the viewpoint, for example, of lightening the burden on patients at the time of administration and of medical economy, a taxol derivative which can be orally administered is in demand.

As a result of extensive investigation to obtain a taxol derivative which can ensure high safety suited for oral administration while maintaining a high antitumor activity and improving the toxicity problem, the present inventors have conducted extensive studies and obtained a compound (hereinafter, referred to as "compound B") of the following formula (B) capable of showing a significant antitumor activity even by its oral administration for example in an antitumor test using mice.

(B)

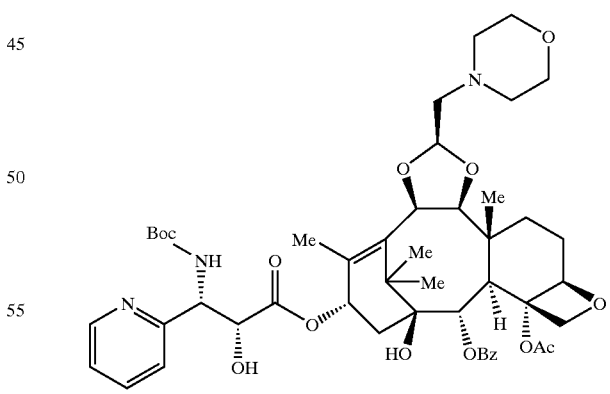

The toxicity problem of this compound was improved in comparison with the compounds disclosed in Examples of JP-A-9-12578. However, its applicability to oral administration in human was not able to be assured, because it was revealed by an in vitro metabolism test using human liver microsome that this compound undergoes its metabolism rapidly in human liver microsome.

DISCLOSURE OF INVENTION

With the aim of inhibiting modification of compounds by their metabolism, the inventors have carried out a new drug design study and found that a compound in which a substituent group is introduced into pyridine ring of the 13-position side chain hardly undergoes its metabolism in human liver microsome and can ensure safety suited for oral administration, while maintaining its antitumor activity and also improving the toxicity problem, thus resulting in the accomplishment of the invention.

Accordingly, the invention provides a compound represented by the following formula (I) or a salt thereof, a medicament which comprises the compound of the following formula (I) or a salt thereof and an antitumor agent which contains the compound of the following formula (I) or a salt thereof.

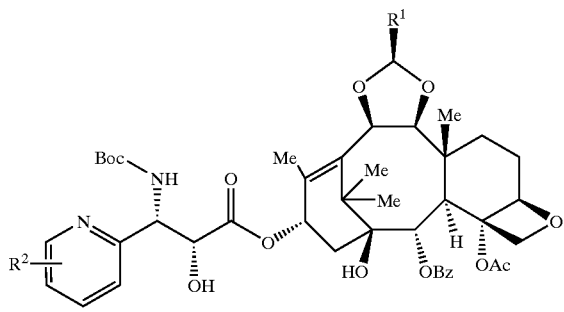

(I)

The invention also provides an intermediate (hereinafter, referred to as "intermediate of the invention") represented by the following formula (III) for use in the production of the taxol derivative, and use thereof.

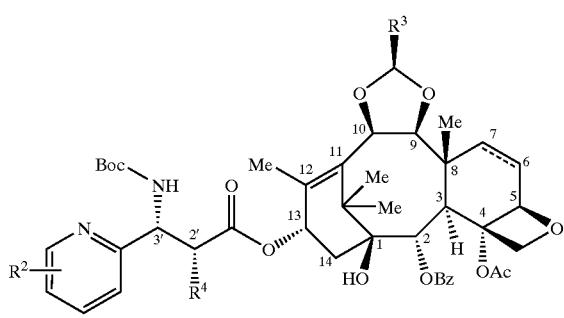

(III)

In the following formula (I), $R^1$ is dimethylaminomethyl group or morpholinomethyl group and $R^2$ is a halogen atom or an alkoxy group having from 1 to 6 carbon atoms. Preferred examples of $R^2$ include methoxy group, fluorine atom and chlorine atom, more preferably fluorine atom and methoxy group.

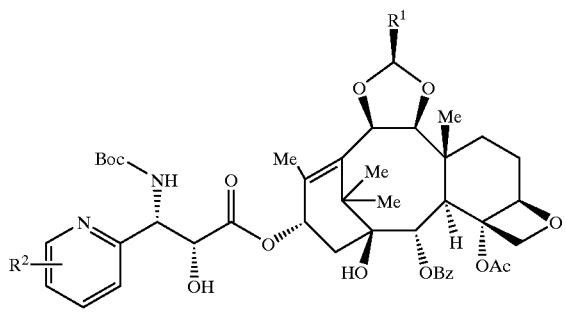

(I)

Particularly preferred is a compound represented by the following formula (II), namely (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-hydroxypropionate, or a salt thereof.

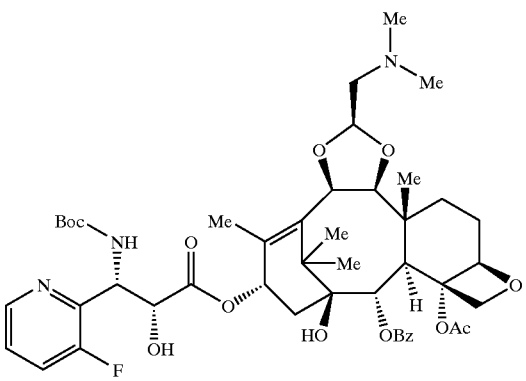

(II)

Also in the above-mentioned intermediate of formula (III), $R^3$ is dimethylaminomethyl group, morpholinomethyl group or vinyl group, $R^4$ is hydroxyl group which may have a protecting group and $R^5$ is an alkoxy group having from 1 to 6 carbon atoms or a halogen atom. In addition, the part of dotted line between the 6-position and 7-position of a partial structure in the intermediate of formula (III), shown by formula:

means that the bond of the part may be a double bond.

In the intermediate of formula (III), examples of the protecting group of $R^4$ include a trialkylsilyl group, benzyl group, a substituted benzyl group, 1-ethoxyethyl group, benzyloxycarbonyl group and 2,2,2-trichloroethoxycarbonyl group. Preferred among them are a trialkylsilyl group such as triisopropylsilyl group, tertiary butyldimethylsilyl group or triethylsilyl group and benzyl group, and particularly preferred are triisopropylsilyl group and benzyl group.

The production intermediate of the taxol derivative of the invention can be used by optionally selecting it in response to the final product of interest. For example, for the production of a compound represented by formula (II):

(II)
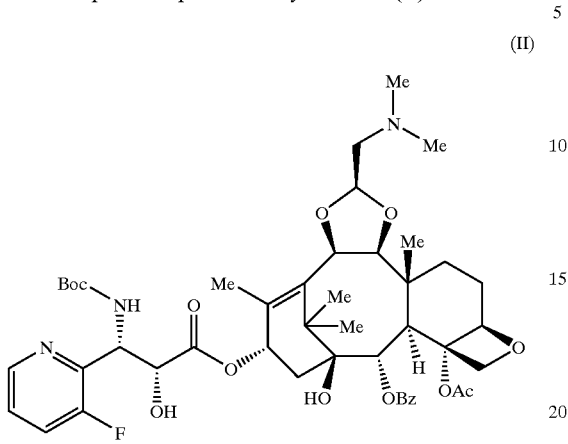

or a salt thereof, it is desirable to use a compound represented by formula (IV):

(IV)
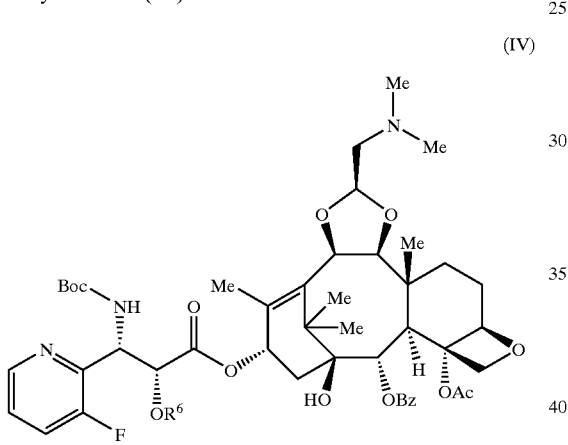

(wherein $R^6$ is triisopropylsilyl group, tertiary butyldimethylsilyl group, triethylsilyl group or benzyl group) or a salt thereof, a compound represented by formula (V):

(V)
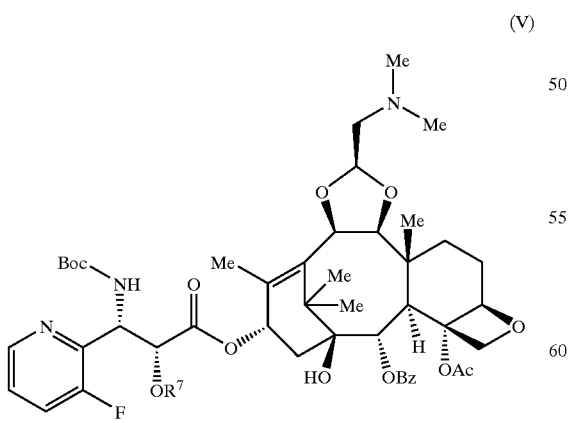

(wherein $R^7$ is triisopropylsilyl group, tertiary butyldimethylsilyl group, triethylsilyl group or benzyl group) or a salt thereof, or a compound represented by formula (VI):

(VI)
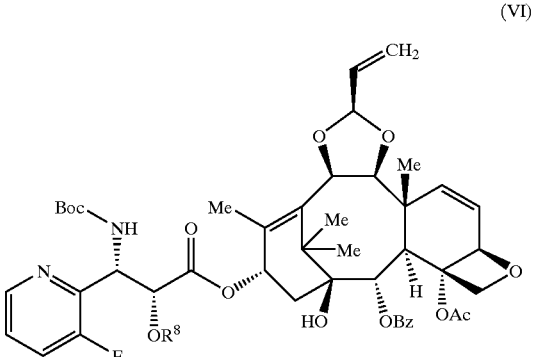

(wherein $R^8$ is triisopropylsilyl group, tertiary butyldimethylsilyl group, triethylsilyl group or benzyl group) or a salt thereof.

Compound (I) can be synthesized through the following steps 1), 2), 3), 4) and 5):

1) a step of reacting a compound of formula (III'):

(III')
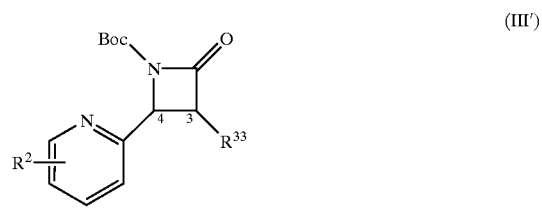

with a compound formula (IV'):

(IV')
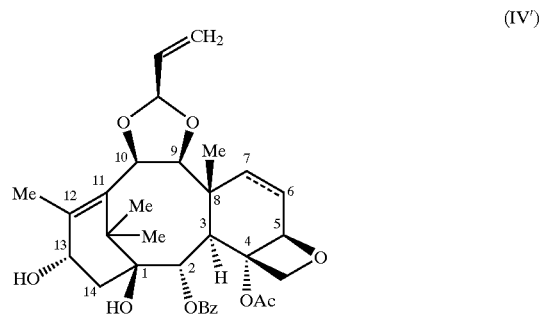

thereby obtaining a compound of the following formula (VI');

(VI')
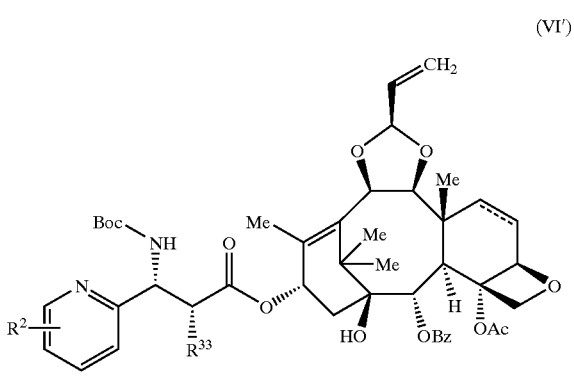

2) a step of converting the vinyl group of the resulting compound (VI') into an aldehyde group;

3) a step of converting the aldehyde group into a dimethylaminomethyl or morpholinomethyl group;
4) a step converting, when the bond between the 6-carbon atom and 7-carbon atom is a double bond, the bond into a single bond; and
5) a step of removing, when $R^{33}$ is hydroxyl group having a protecting group, the protecting group.

In compound (III'), $R^{33}$ means hydroxyl group which may have a protecting group. Here, $R^{33}$ at the 3-position on the β-lactam ring is in a cis configuration relative to the pyridyl group at the 4-position. Examples of the protecting group of $R^{33}$ include substituted silyl, benzyl, substituted benzyl, 1-ethoxyethyl, benzyloxycarbonyl and 2,2,2-trichloroethoxycarbonyl groups. The substituted silyl group has, for example, an alkyl group, an aryl group or an aralkyl group as a substituent. Examples of the substituted silyl group include trimethylsilyl, triisopropylsilyl, isopropyldimethylsilyl, tert-butyldimethylsilyl, tribenzylsilyl and tert-butyldiphenylsilyl groups. The substituted benzyl group has, for example, a halogen atom, an alkyl group, an alkoxy group or a nitro group as a substituent and examples of the substituted benzyl group include paranitrobenzyl and paramethoxybenzyl groups. Preferred examples of the protecting group of $R^{33}$ include trialkylsilyl groups such as triisopropylsilyl, tert-butyldimethylsilyl and triethylsislyl, and benzyl group, with the triisopropylsilyl and benzyl groups being especially preferred.

Compound (III') may be a racemic compound or an optically active compound (VII') represented by formula (VII'):

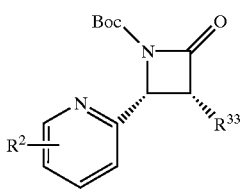
(VII')

The bond between the 6-carbon atom and 7-carbon atom of a partial structure, of compound (IV'), represented by formula (V'):

(V')

may be either a single bond or a double bond.

Compound (VII') and compound (III') are prepared by the following invention processes, respectively:

The optically active compound (VII'):

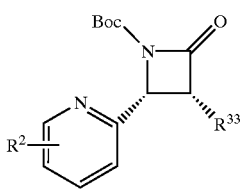
(VII')

is prepared by reacting a compound of formula (VIII'):

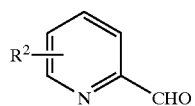
(VIII')

with a compound formula (IX'):

$R^{44}—NH_2$  (IX')

reacting a resulting compound of formula (X'):

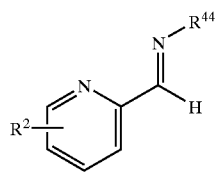
(X')

with a compound of formula (XI'):

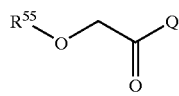
(XI')

to obtain a compound of formula (XII')

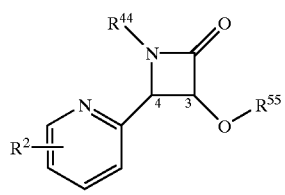
(XII')

deprotecting the hydroxyl group at the 3-position on the β-lactam ring as needed, introducing a protecting group to the hydroxyl group as needed, removing $R^{44}$ which is a protecting group of the nitrogen atom in the β-lactam ring, optically resolving a resulting racemic compound (XIII'):

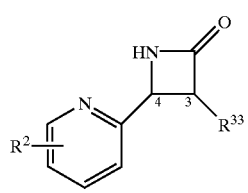
(XIII')

and introducing t-butoxycarbonyl group into the nitrogen atom in the β-lactam ring.

A racemic compound (III') can be prepared by reacting compound (VIII') with compound (IX'), reacting the resulting compound (X') with compound (XI'), thereby obtaining compound (XII'), deprotecting the hydroxyl group at the 3-position on the β-lactam ring as needed, introducing a protecting group to the hydroxyl group as needed, and introducing t-butoxycarbonyl group to the nitrogen atom in the β-lactam ring.

The above-described $R^2$ represents a halogen atom or an alkoxy group having 1 to 6 carbon atoms, with methoxy group and fluorine atom being preferred.

The above-described $R^{33}$ represents hydroxyl group which may have a protecting group, with triisopropylsilyloxy group being preferred.

The above-described $R^{44}$ represents hydrogen atom, hydroxyl group, an alkoxy group having from 1 to 6 carbon atoms which may have substituent(s), an alkanoyl group having from 1 to 6 carbon atoms which may have substituent(s), an alkenoyl group having from 2 to 6 carbon atoms which may have substituent(s), an aryl group which may have substituent(s), an aryloyl group which may have substituent(s), an aralkyl group which may have substituent(s) or a substituted silyl group. The substituted silyl group has, for example, an alkyl group, an aryl group or an aralkyl group as a substituent. Examples of the substituted silyl group include trimethylsilyl, triisopropylsilyl, isopropyldimethylsilyl, tert-butyldimethylsilyl, tribenzylsilyl and tert-butyldiphenylsilyl groups.

The aryl group which may have substituent(s), the aryloyl group which may have substituent(s) and aralkyl group which may have substituent(s) each has, for example, a halogen atom, an alkyl group having from 1 to 6 carbon atoms, an halogenoalkyl group having from 1 to 6 carbon atoms, an alkoxy group having from 1 to 6 carbon atoms, nitro group, carbamoyl group or cyano group as a substituent. These aryl, aryloyl and aralkyl groups may each have one or more of the above-exemplified substituents.

As $R^{44}$, a phenyl group which may have substituent(s) and an aralkyl group which may have substituent(s) are preferred. An alkoxy group is preferred as a substituent. As $R^{44}$, 4-methoxyphenyl and bis(4-methoxyphenyl)methyl groups are particularly preferred.

The above-described $R^{55}$ represents a protecting group of hydroxyl group. No particular limitation is imposed so long as it is used generally in this art without exerting any unfavorable influences on the step of producing compound (XII'). As $R^{55}$, an acyl group which may have substituent(s) is preferred and an acetyl group is particularly preferred.

The above-described Q represents a halogen atom such as fluorine atom, chlorine atom, bromine atom and iodine atom, preferably chlorine atom.

Optical resolution of compound (XIII') is conducted, for example, by the method using an optically active column.

The compound of the present invention can be synthesized in accordance with the method reported in JP-A-9-12578, for example, the following synthetic methods. In this connection, the reaction may be carried out by protecting substituents with protecting groups as occasion demands, but the operating order of their deprotection is not particularly limited.

Synthetic Method 1:

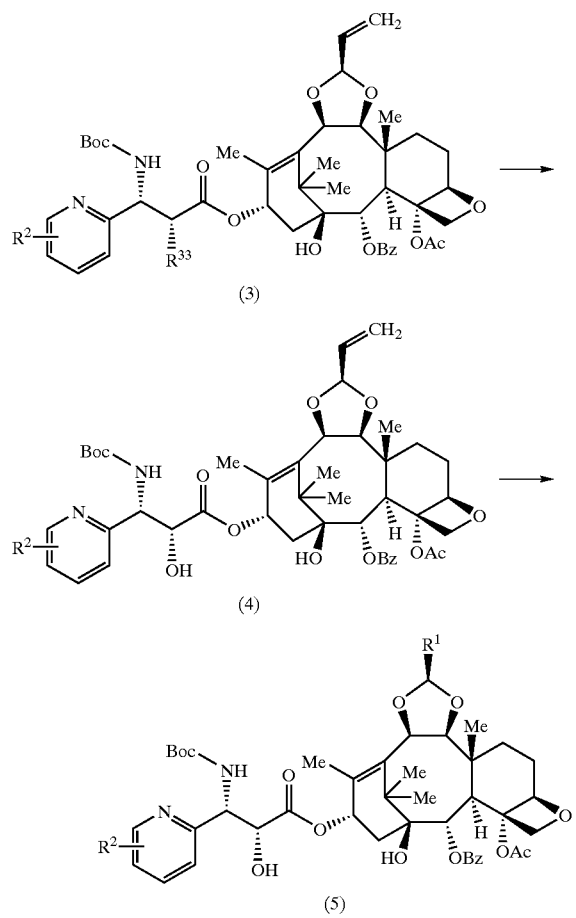

Compound (3) is obtained by condensing compound (1) with compound (2) in the presence of a base. Then, a protecting group of the hydroxyl group of the thus obtained compound (3) is removed to give compound (4). The terminal olefin thereof is converted into a diol using an oxidizing agent such as N-methylmorpholine-N-oxide in the presence of an osmium tetraoxide catalyst and then cleaved oxidatively using sodium periodate and the like to form an aldehyde. Thereafter, a reductive reaction with the corresponding amine is carried out to obtain compound (5).

Synthetic Method 2:

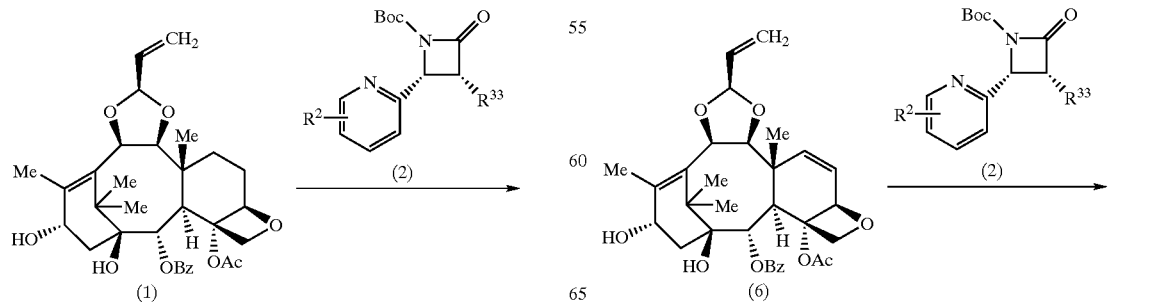

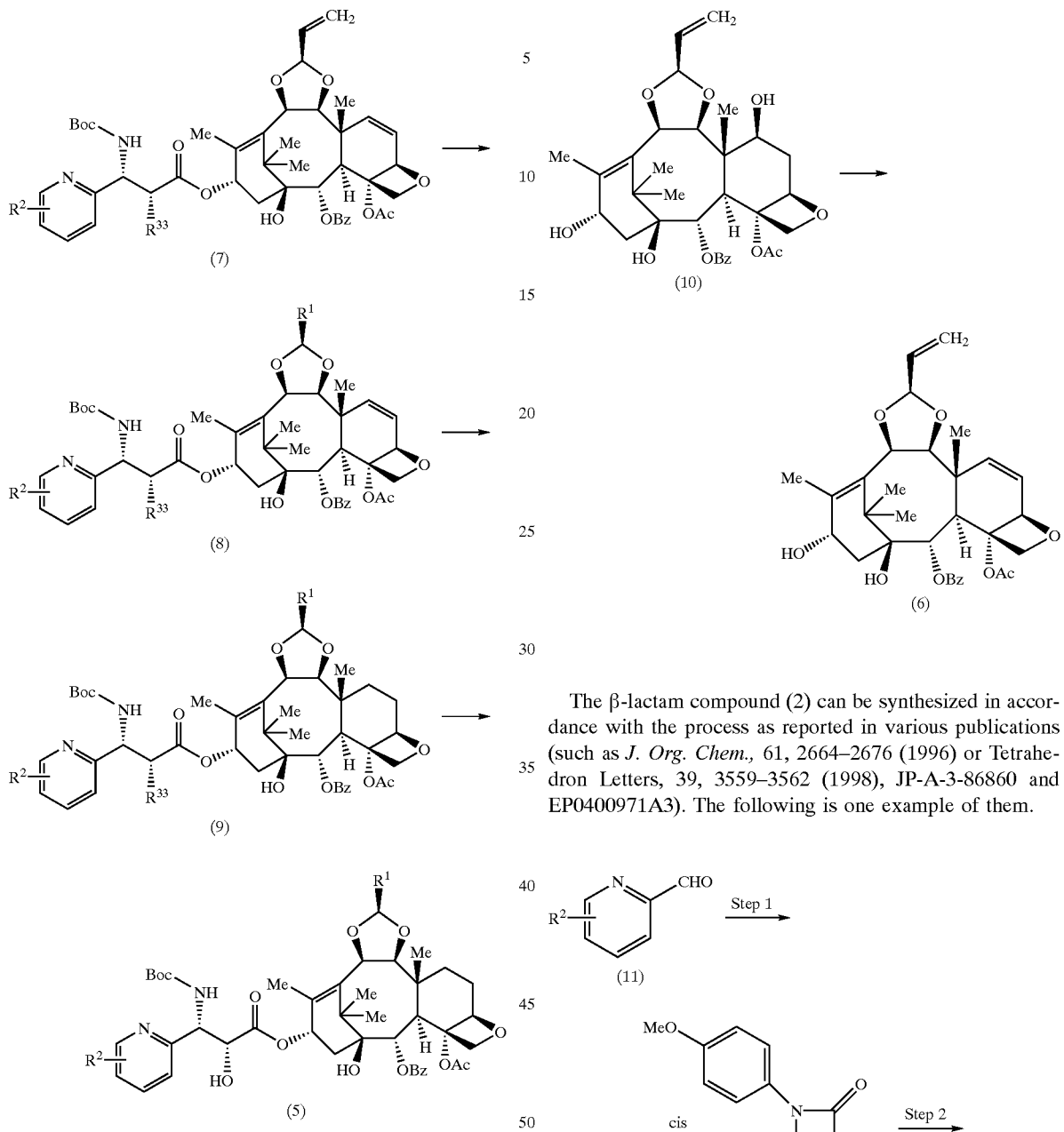

Compound (7) is obtained by condensing compound (6) with a compound (2) in the same manner as in Synthetic Method 1. Then compound (8) can be obtained by the conversion of the terminal olefin thereof in the same manner as in Synthetic Method 1. Thereafter, compound (9) is obtained by reducing the olefin at the 6 and 7-positions by the hydrogenation, and then a protecting group on the hydroxyl group is finally removed, thereby obtaining compound (5).

With regards to compounds (1) and (6) serving as starting materials, the synthesis method of the former one is described in JP-A-9-12578, while the latter one can be synthesized by one step from compound (10) described in JP-9-A-12578.

The β-lactam compound (2) can be synthesized in accordance with the process as reported in various publications (such as *J. Org. Chem.*, 61, 2664–2676 (1996) or Tetrahedron Letters, 39, 3559–3562 (1998), JP-A-3-86860 and EP0400971A3). The following is one example of them.

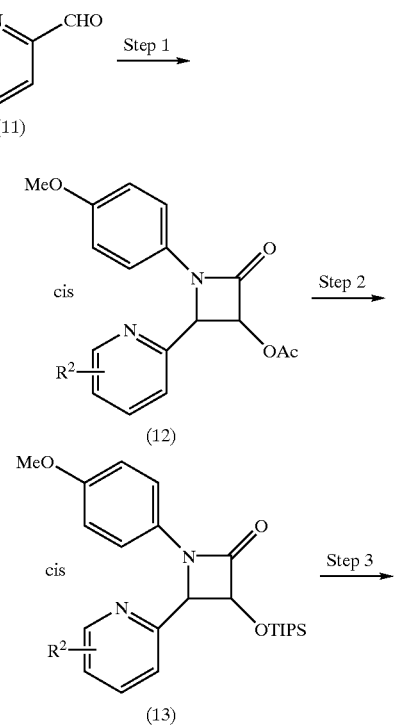

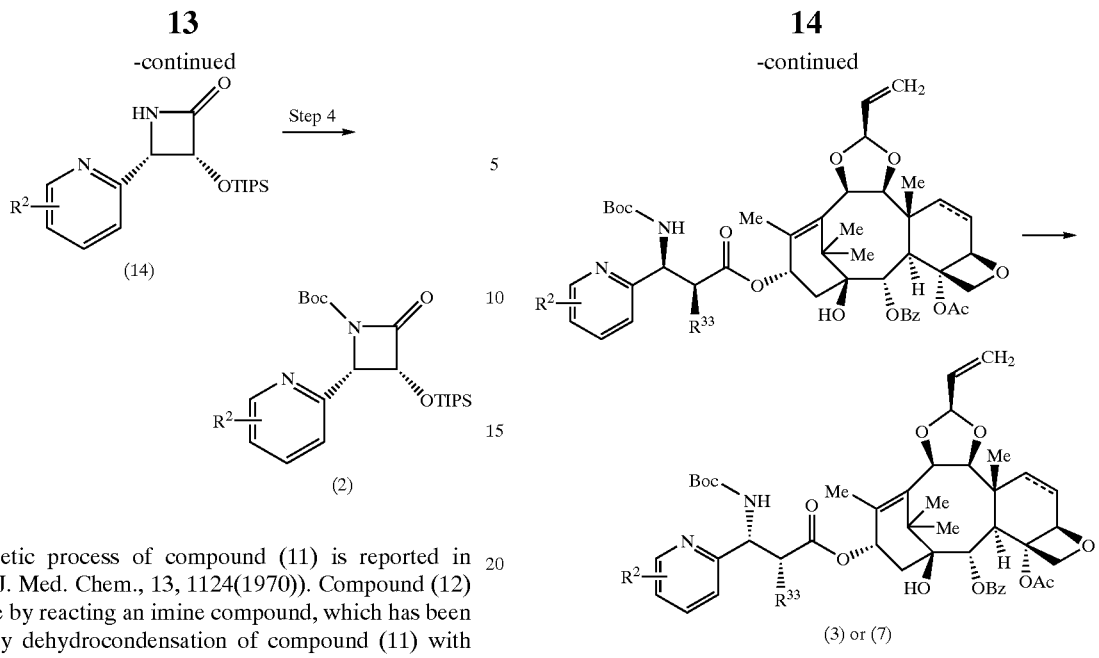

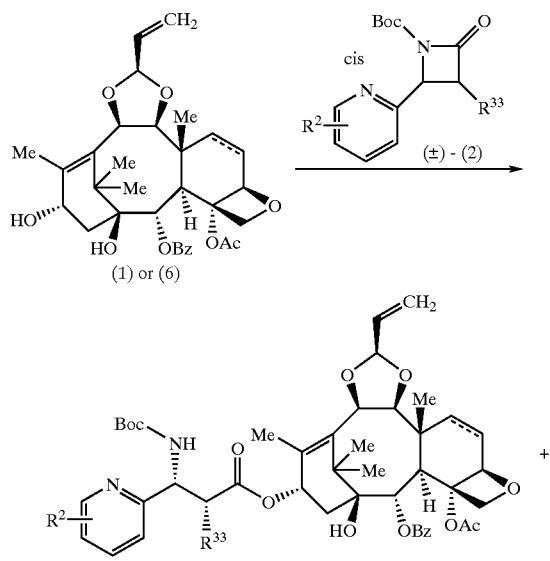

A synthetic process of compound (11) is reported in literature (J. Med. Chem., 13, 1124(1970)). Compound (12) is available by reacting an imine compound, which has been obtained by dehydrocondensation of compound (11) with p-anisidine, with acetoxyacetyl chloride in the presence of a base (which is known as Staudinger Reaction). Compound (13) is available by treating compound (12) with a base in a methanol solvent, thereby removing an acetyl group, and then reacting the resulting compound with triisopropylsilyl chloride in the presence of imidazole. By acting cerium (IV) ammonium nitrate on compound (13), a racemic modification of compound (14) can be obtained. This racemic compound is then resolved by chromatography on an optically active column, whereby compound (14) having a steric configuration as illustrated above can be obtained. In the end, by acting di-tert-butyl dicarbonate on compound (14), compound (2) can be obtained.

Alternatively, compound (3) or (7) having a desired steric configuration is available by condensing compound (1) or (6) with an excess amount of the racemic modification of compound (2) without conducting optical resolution during the synthesis of compound (2), and then separating the resulting diastereomer by chromatography on a silica gel column.

In the above-described synthetic processes, $R^1$, $R^2$ and $R^{33}$ have the same meanings as described above. Abbreviations Boc, Me, Ac, Bz and TIPS mean tertiary butoxy carbonyl group, methyl group, acetyl group, benzoyl group and triisopropylsilyl group, respectively.

Each reaction will next be described more specifically.

Synthesis of Imine (X')

Mixing of aldehyde (VIII') with amine (IX') in a solvent or in a solvent-free manner generates a mixture of imine (X') and water separated therefrom. The separated water can be removed by adding to the reaction mixture a dehydrating agent such anhydrous sodium sulfate, calcium chloride or molecular sieves and then filtering the mixture. Alternatively, water can be removed by using an azeotropic mixture-forming solvent with water such as toluene or benzene and evaporating it under reduced pressure (if necessary, the above-described procedure, that is, addition of a solvent and evaporation under reduced pressure, is repeated). No particular limitation is imposed on the solvent to be used for this reaction and toluene, benzene and methylene chloride and mixed solvents thereof can be mentioned as examples. The reaction temperature usually ranges from −20° C. to 150° C. or the boiling point of the solvent, preferably ranges from 0° C. to 100° C. or the boiling point of the solvent.

Synthesis of β-Lactam (XII'):

It can be synthesized by dissolving imine (X') and a base such as tertiary amine typified by triethylamine in a solvent and then adding a solution of acid halide (XI') at room temperature or lower (preferably 0° C. or lower). The solution of acid halide (XI') is preferably added dropwise. It is presumed that in this reaction, ketene once formed by the reaction between the acid halide and the base is reacted with the imine, whereby a β-lactam ring is constructed while selecting a cis configuration. With regards to the steric configuration in the reaction constructing a β-lactam ring, it is known that selectivity changes depending on reaction conditions or the structure of the imine or acid halide. Accordingly, intended cis configuration is available selectively by selecting reaction conditions properly according to the kind of $R^2$, $R^{44}$ or $R^{55}$. Examples of the solvent used for the reaction include methylene chloride, toluene and benzene, and mixed solvents thereof. Although no particular limitation is imposed, a dry solvent is preferred. The reaction temperature after dropwise addition usually ranges from −78° C. to 100° C. or the boiling point of the solvent, with a range of from −78° C. to room temperature being preferred.

3-Protecting Group Exchanging Reaction

Reaction conditions differ with the kind of $R^{55}$ and $R^{33}$. When $R^5$ represents a benzyl group or a trialkylsilyl group, it is possible to carry out the subsequent step without exchanging the protecting group with another group. Deprotecting reaction of $R^{55}$ can be carried out under ordinary reaction conditions. The following is an example wherein $R^{55}$ represents an acetyl group. A compound having a hydrogen atom as $R^{55}$ is available, for example, by dissolving compound (XII') in a solvent and adding a base such as potassium carbonate in an amount sufficient for reaction. Examples of the solvent usable for this reaction include methanol, tetrahydrofuran and methylene chloride, and mixed solvents thereof. No particular limitation is imposed, but a dry solvent is preferred. The reaction temperature usually ranges from −78° C. to 100° C. or the boiling point of the solvent, with a range of from 0° C. to room temperature being preferred. The subsequent protection of a hydroxyl group can be carried out in a conventional manner, though reaction conditions differ with the kind of $R^{33}$. The following is an example wherein $R^{33}$ represents a trialkylsilyloxy group such as triisopropylsilyloxy group. A trialkylsilyloxy compound is available by dissolving a starting material in a solvent and then adding an amine type base or another base (imidazole is known to be preferable as a base for silylation reaction) and a trialkylsilyl chloride such as triisopropylsilyl chloride. Examples of the solvent usable for this reaction include methylene chloride, dimethylformamide and tetrahydrofuran, and mixed solvents thereof. No particular limitation is imposed, but a dry solvent is preferred. The reaction temperature usually ranges from −78° C. to 100° C. or the boiling point of the solvent, with a range of from 0° C. to room temperature being preferred.

Deprotection of N-protecting Group $R^{44}$ is a protecting group of the nitrogen atom at the 1-position of the β-lactam ring. Examples thereof include substituted phenyl type protecting groups such as 4-methoxyphenyl (anisyl) group and 2,4-dimethoxyphenyl group, aryl-substituted methyl type protecting groups such as 2,4-dimethoxybenzyl group and bis(4-methoxyphenyl) methyl group and trialkylsilyl type protecting groups such as tert-butyldiphenylsilyl group. Deprotection can be carried out in a conventional manner according to the kind of $R^{44}$. The following is an example of 4-methoxyphenyl group. Compound (XIII') is available by dissolving or suspending the trialkylsilyloxy compound obtained in the above-described section in a solvent and adding an oxidizing agent such as cerium (IV) ammonium nitrate or an aqueous solution thereof to the resulting solution or suspension. Examples of the solvent usable for this reaction include water, acetonitrile, acetone and tetrahydrofuran, and mixed solvents thereof. Of these, organic solvents miscible with water at any ratio or mixed solvents of the organic solvent and water are preferred. The reaction temperature usually ranges from −78° C. to 100° C. or the boiling point of the solvent, preferably from −20° C. to room temperature and more preferably from −5° C. to 5° C.

Introducing Reaction of Boc Group

Compound (III') is available by dissolving compound (XIII') in a solvent and then adding di-tert-butyl dicarbonate to the resulting solution in the presence of a base such as 4-dimethylaminopyridine. Examples of the solvent usable for this reaction include methylene chloride and tetrahydrofuran, and mixed solvents thereof. No particular limitation is imposed, but a dry solvent is preferred. The reaction temperature usually ranges from −78° C. to 100° C. or the boiling point of the solvent, with a range of from 0° C. to room temperature being preferred.

Condensation Reaction Between Compounds (III') and (IV')

Compound (III') and (IV') are dissolved in a solvent, followed by the addition of a base such as lithium hexamethyl disilazide, sodium hexamethyl disilazide, sodium hydride or potassium tert-butoxide at −78° C. to room temperature (the preferred temperature differs with the kind of the above-exemplified base added, but cooling is preferred). Alternatively, after addition of the base to one of the solutions of compound (III') or (IV'), the other one may be added to the mixture. These procedures are preferably conducted under the conditions having a low water content. Then, reaction is conducted at the temperature employed upon mixing or at a temperature increased to the vicinity of room temperature, whereby compound (VI') can be obtained. Examples of the solvent usable here include methylene chloride and tetrahydrofuran and mixed solvents thereof. No particular limitation is imposed, but a dry solvent is preferred.

Reaction to Introduce Compound (VI') to (I)

Step of converting vinyl group of Compound (VI') to aldehyde group: Compound (VI') is dissolved in tetrahydrofuran, acetone, butanol, acetonitrile or water, or a mixed solvent thereof (hydrous solvent is preferred). The resulting solution is then reacted with an oxidizing agent, such as osmium tetraoxide or potassium osmate, for converting an olefin to the corresponding diol, or a catalytic amount of osmium tetraoxide is added to the resulting solution in the presence of an oxidizing agent such as N-methylmorphlin-N-oxide, whereby a compound having an olefin portion converted to the corresponding diol can be obtained. The resulting diol compound is dissolved in tetrahydrofuran, methanol, ethanol, acetonitrile or water, or a mixed solvent thereof (preferably, a hydrous solvent), followed by the addition of an oxidizing agent, such as sodium metaperiodate, for causing oxidative cleavage of 1,2-diol, whereby a compound having an aldehyde group is available as a result of conversion. This step can also be carried out in one pot by adding sodium metaperiodate or solution thereof to the reaction mixture after diol-introducing reaction. The reaction temperature usually ranges from −78° C. to 100° C. or the boiling point of the solvent, preferably a temperature in the vicinity of room temperature.

Step for converting aldehyde group to dimethylamino or morpholino group: The aldehyde compound obtained above is dissolved in a solvent, followed by the addition of either one of dimethylamine or morpholine, an acid such as acetic acid, and a reducing agent such as sodium cyanoborohydride or sodium triacetoxyborohydride, whereby the aldehyde group can be converted into dimethylaminomethyl or morpholinomethyl group. Examples of the solvent usable for this reaction include ethanol and tetrahydrofuran, and mixed solvents thereof. Although no particular limitation is imposed on the solvent, those capable of dissolving therein, until completion of the reaction, a reducing agent in an amount necessary for completing the reaction is preferred. The reaction temperature usually ranges from −78° C. to 100° C. or the boiling point of the solvent, with a temperature in the vicinity of room temperature being preferred.

A step for reducing the double bond, if the part represented by formula (V') is a double bond, to a single bond:

The dimethylamino or morpholinomethyl compound obtained above is dissolved in a solvent, followed by the addition of a reducing catalyst such as palladium carbon, platinum carbon or ruthenium carbon. The resulting mixture is stirred under a hydrogen atmosphere or in the presence of a hydrogen source such as formic acid or ammonium formate, whereby a compound having a single bond formed by reducing the double bond can be obtained. Examples of the solvent usable for this reaction include water, alcohols such as methanol and ethanol, tetrahydrofuran and ethyl acetate, and mixed solvents thereof. Although no particular limitation is imposed on the solvent, polar solvents are preferred. The reaction temperature usually ranges from −78° C. to 100° C. or the boiling point of the solvent, preferably a temperature in the vicinity of room temperature.

A Step for removing $R^{33}$: Deprotection conditions differ with the kind of $R^{33}$. The following is an example wherein $R^{33}$ represents a trialkylsilyloxy group such as triisopropylsilyloxy group. The deprotection can be carried out by dissolving the above-obtained reductant compound in a solvent such as tetrahydrofuran and reacting the resulting solution with a quarternary ammonium fluoride such as tetrabutylammonium fluoride. The reaction temperature preferably ranges from the vicinity of 0° C. to room temperature. Alternatively, the deprotection may be carried out by using a complex of hydrogen fluoride and pyridine in a pyridine solvent. Examples of the solvent usable for this reaction include tetrahydrofuran, but it is not limited thereto. The reaction temperature usually ranges from −78° C. to 100° C. or the boiling point of the solvent, preferably from −5° C. to room temperature.

Synthetic Process of Compound (IV'):

[When C6–C7 is a double bond] 10-O-deacetyl baccatine III is dissolved in a solvent and the resulting solution is reacted with a reducing agent such as tetrabutylammonium borohydride, whereby a compound having a β-hydroxyl group at the 9-position can be obtained as a result of reduction. The resulting compound is dissolved in a solvent and the resulting solution is reacted with an acrolein acetal typified by diethyl acetal in the presence of a strong acidic compound such as camphor-sulfonic acid or p-toluenesulfonic acid, a salt of such an acid with a tertiary amine typified by triethylamine, or a compound functioning as a Lewis acid such as zinc chloride, whereby compound (IV') having hydroxyl group at the 7-position can be obtained. The resulting compound is dissolved in a solvent and the resulting solution is reacted with trifluoromethanesulfonic anhydride in the presence of a base such as 4-dimethylaminopyridine, whereby dehydration proceeds, making it possible to obtain compound (IV'). Examples of the solvent usable for this reaction include, but not limited to, methylene chloride and dichloroethane, and mixed solvents thereof. The reaction temperature usually ranges from −78° C. to 100° C. or the boiling point of the solvent, preferably from −5° C. to room temperature.

[When C6–C7 is a single bond] A compound obtained by substituting hydrogen atom for the 7-positioned hydroxyl group of 10-O-deacetyl baccatine III is known. This compound is dissolved in a solvent such as tetrahydrofuran. The resulting solution is reacted with a borane complex such as borane-tetrahydrofuran complex or diborane, whereby a compound having the 9-positioned ketone reduced to β-hydroxyl group can be obtained. The resulting compound is dissolved in a solvent such as methylene chloride or dichloroethane. The resulting solution is reacted with an acrolein acetal typified by diethyl acetal in the presence of a strong acidic compound such as camphor-sulfonic acid or p-toluenesulfonic acid, a salt of such a compound with a tertiary amine typified by triethylamine, or a compound functioning as a Lewis acid such as zinc chloride, whereby compound (IV') can be obtained. The reaction temperature usually ranges from −78° C. to 100° C. or the boiling point of the solvent, preferably from −5° C. to room temperature.

The compound of the invention may be in its free form or an acid addition salt. Examples of the acid addition salt include inorganic acid salts such as hydrochloride, sulfate, nitrate, hydrobromide, hydroiodide and phosphate or organic acid salts such as acetate, methane sulfonate, benzenesulfonate, toluenesulfonate, citrate, maleate, fumarate and lactate. It may also be in the form of a hydrate or a solvate, and examples of the solvent include water, methanol, ethanol, propanol, butanol, acetone, acetonitrile, benzene, toluene, tetrahydrofuran and N,N-dimethylformamide.

In addition, the medicament of the invention can realize treatment of cancers based on its antitumor action, and examples of the object to be treated include various cancers such as lung cancer, gastrointestinal cancer, ovarian cancer, uterine cancer, breast cancer, cancer of liver, cancer of head and neck, blood cancer, renal cancer and testicular tumor.

The compound of the invention can be administered as various injections such as for intravenous injection, intramuscular injection and subcutaneous injection, or by various methods such as oral administration and percutaneous administration. Among these administration methods, oral administration is desirable from the viewpoint of achieving the effects which will be described later. In the case of oral administration, it may be any of free compound or salts. When a test was carried out using cancer-free mice, the compound of the invention showed no renal toxicity.

Applicability of the compound of the invention as an oral preparation can be predicted by an in vitro test which uses human liver microsome. In the case of oral administration, the drug dissolves in the gastrointestinal tract, undergoes its metabolism in the digestive tract and liver and then enters into the blood circulation system. Accordingly, it is considered that metabolism of the drug in the liver exerts influence on the expression of efficacy of the drug. Particularly, it is predicted that the compound of the invention and its analogous compounds undergo their metabolism by CYP3A which is an enzyme distributed in the liver microsome. Thus, prediction of the metabolism by an in vitro test using liver microsome is important in considering its clinical use in practice. It has been reported, for example in *Pharm. Tech. Japan*, 13, 17–39, 1997 and *J. Pharmacol. Exp. Ther.*, 283, 46–58, 1997, that predicted values of the metabolism by in vitro tests using liver microsome almost coincide with the measured values in human clinical tests. The human liver microsome is available for example from Xenotech LLC, and measurement of the metabolic rate can be carried out making reference to the above journals.

When the drug metabolism rate in liver microsome is measured, bioavailability of the drug can also be calculated as a theoretical value (*J. Pharmacol. Exp. Ther.*, 283, 46–58, 1997). Bioavailability is defined as the amount and rate of a drug which reaches the systemic circulating blood, relative to the administered drug (Pharmacokinetic Studies on Drug Development, edited by Yuichi Sugiyama, p. 15, published by Yakuji Jiho). In the case of oral administration, there are various obstacles until a drug enters into the circulating blood, such as dissolution in the gastrointestinal tract, passage through the digestive tract mucous membrane and metabolism in the digestive tract and liver. Thus, it is considered that the range of variability of its final blood concentration, namely bioavailability, among individuals becomes large in comparison with the case of its direct administration into circulating blood. Hellriegel et al. have examined bioavailability value and its individual variability (CV value) on 149 articles of various drugs on the market and reported that there is a negative correlation between them (*Clin. Pharmacol. Ther.*, 60, 601–607, 1996). That is, it is known that the range of variability of bioavailability among individuals becomes large as the value of bioavailability becomes small.

In the case of antitumor agents, they are administered mostly at around the maximum tolerated dose in order to increase response rate, so that the therapeutic range and the toxicity range draw close to each other and the safety range becomes narrow as the result. Thus, it becomes difficult to use a drug having a large variability range of individual bioavailability as an antitumor agent.

According to the compound of the invention, its metabolic rate in human liver microsome was reduced, and the theoretical value of bioavailability of its unchanged form was also improved. Thus, it was predicted that the variability range of bioavailability values of the unchanged compound among individuals would be small. Because of this effect, it is sufficiently possible to carry out oral administration of the compound of the invention from the safety point of view in enlarging safety range and from viewpoint of effective drug efficacy expression. In this connection, theoretical bioavailability value of the unchanged compound is preferably 0.4 or more, more preferably 0.7 or more.

In addition, applicability of the compound of the invention as oral preparations can also be predicted by a bioavailability (BA) test using monkeys. Metabolism of the compound of formula (B) by the liver microsome of mouse and dog is slow, and its oral absorption property is actually excellent. On the other hand, its metabolism by the monkey liver microsome is quick similar to the case of the human liver microsome. In this case, oral absorption property of the compound of formula (B) in monkey is low. On the contrary, metabolism of the compound of the invention by the monkey liver microsome is slow similar to the case of the mouse and dog liver microsome. Thus, when bioavailability (BA) was measured using monkeys for the purpose of confirming the oral absorption improving effect by the inhibition of metabolism, it was confirmed that the oral absorption in monkey was sharply improved by the compound of the invention in comparison with the compound of formula (B).

Regarding the method for the preparation of pharmaceutical preparations of medicaments and antitumor agents, they can be prepared by selecting appropriate pharmaceutical preparation in response to its administration method and employing a usually used preparation method. Among dosage forms of the antitumor agent of the invention, tablets, powders, granules and capsules can be exemplified as the preparations for oral administration use. Examples of other dosage forms include solutions, syrups, elixirs and oily or aqueous suspensions. Among them, capsules, tablets and solutions are desirable. In the case of injections, additives such as a stabilizer, an antiseptic and a solubilization assisting agent can be used in the preparation. When a solution which may contain such auxiliary substances is made into a solid preparation by freeze-drying or the like means, it can be used as a pharmaceutical preparation which is dissolved before use.

Solutions, suspensions and emulsions can be exemplified as the liquid preparation, and additive agents such as a suspending agent and an emulsifying agent can be used when these pharmaceutical preparations are prepared.

The compound of the invention can be used for the treatment of cancers in mammals, particularly in human, and when administered to human, it is desirable to administer it once a day and repeat it at appropriate intervals.

Regarding its dose, it is desirable to administer it within the range of from about 0.5 mg to 50 mg, preferably from about 1 mg to 20 mg, based on 1 $m^2$ of the body surface area.

The invention is described in detail based on the following examples. In the description of the examples, the following abbreviations will be used. Boc means tertiary butoxycarbonyl group, Ac means acetyl group, Bz means benzoyl group, TIPS means triisopropylsilyl group and Bn means benzyl group.

BEST MODE FOR CARRYING OUT INVENTION

EXAMPLE 1

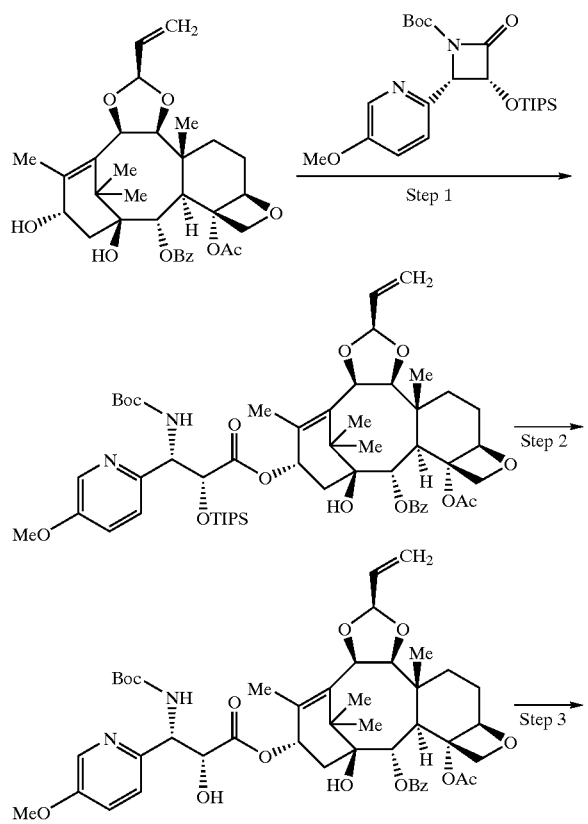

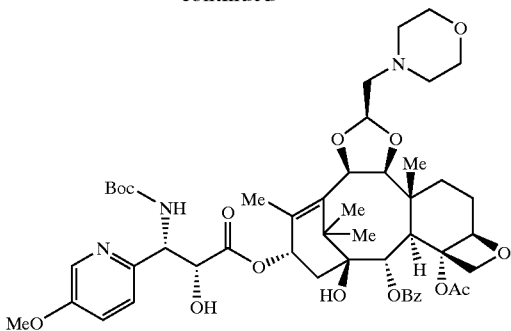

Figure 1:
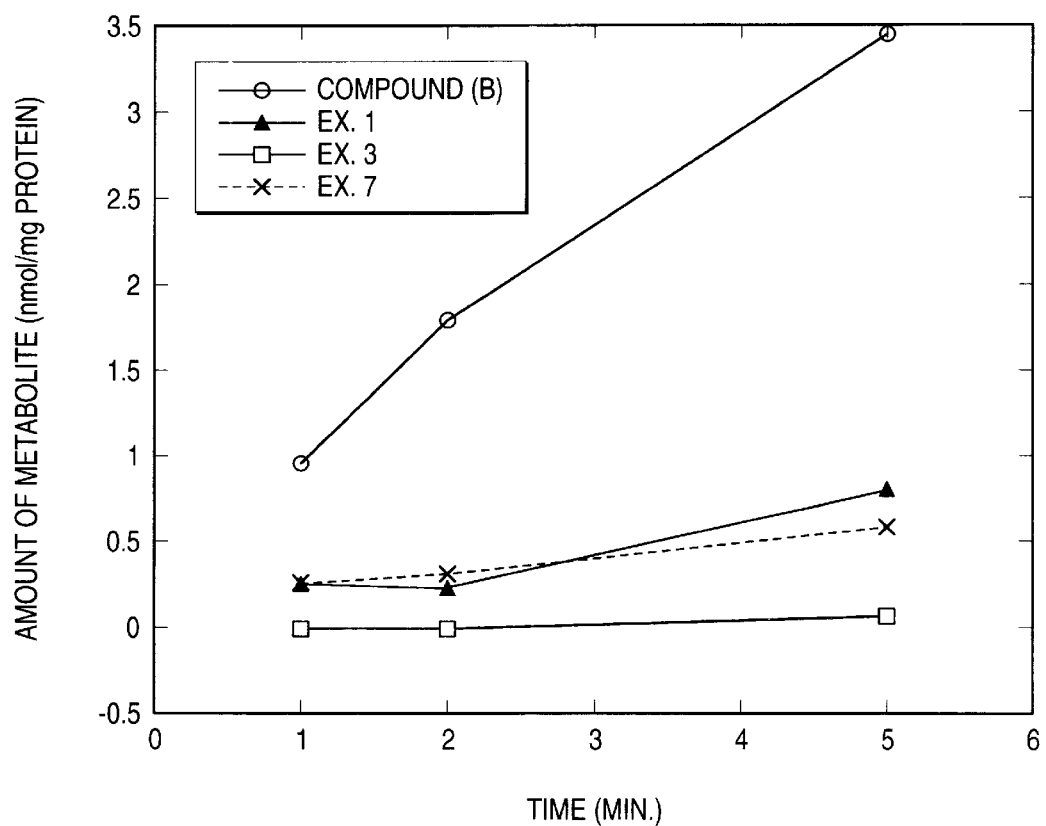
FIG. 1 is a graph showing changes with the passage of time in the amount of metabolite formed from respective compounds.

Step 1: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-3-(5-methoxy-2-pyridyl)-2-triisopropylsilyloxypropionate A 300 mg portion of (1S,2S,3R,4S,5R,8R,9S,10R,13S)-4-acetoxy-2-benzoyloxy-5,20-epoxy-1,13-dihydroxy-9,10-[(1S)-2-propenylidenedioxy]tax-11-ene was dissolved in 10 ml of dry tetrahydrofuran, and the solution was mixed with 0.63 ml of lithium hexamethyldisilazide (1 M tetrahydrofuran solution) at −60° C. and stirred for 25 minutes. A 5 ml portion of tetrahydrofuran solution containing 280 mg of (3R,4S)-1-(tert-butoxycarbonyl)-4-(5-methoxy-2-pyridyl)-3-triisopropylsilyloxy-2-azetidinone was added to the reaction solution at the same temperature, and the mixture was stirred under ice-cooling for 40 minutes. Saturated ammonium chloride aqueous solution and ethyl acetate were added to the reaction solution to carry out separation of layers, and the water layer was extracted with ethyl acetate. The organic layers were combined, washed with saturated brine and then dried with anhydrous sodium sulfate. The solvent was evaporated under a reduced pressure and the resulting residue was purified by a silica gel column chromatography (developing solvent; hexane:ethyl acetate=5:1 (v/v)) to obtain 540 mg of the title compound.

$^1$H-NMR (400 MHz, CDCl$_3$, TMS) δ: 0.89–0.95 (21 H, m), 1.32 (3 H, s), 1.33–1.62 (3 H, m), 1.41 (9 H, s), 1.52 (3 H, s), 1.65 (3 H, s), 1.82 (3 H, s), 1.92–2.32 (3 H, m), 2.49 (3 H, s), 2.98 (1 H, d, J=4.9 Hz), 3.85 (3 H, s), 4.20 (1 H, d, J=7.4 Hz), 4.22 (1 H, d, J=6.8 Hz), 4.32 (1 H, d, J=8.3 Hz), 4.95 (1 H, s), 5.21 (1 H, d, J=5.8 Hz), 5.26–5.29 (2 H, m), 5.39–5.47 (3 H, m), 5.57 (1 H, d, J=17.6 Hz), 5.96–6.02 (2 H, m), 6.11 (1 H, t-like, J=8.3 Hz), 7.15 (1 H, dd, J=2.4, 8.8 Hz), 7.31 (1 H, d, J=8.8 Hz), 7.44 (2 H, t, J=7.8 Hz), 7.56 (1 H, t, J=7.8 Hz), 8.13 (2 H, d, J=7.8 Hz), 8.26 (1 H, d, J=3.0 Hz).

Step 2: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-2-hydroxy-3-(5-methoxy-2-pyridyl)propionate A 530 mg portion of the compound obtained in the above step 1 was dissolved in 10 ml of dry tetrahydrofuran, 1.0 ml of tetrabutylammonium fluoride (1M tetrahydrofuran solution) was added to the solution under ice-cooling and then the mixture was stirred at the same temperature for 30 minutes. Water and ethyl acetate were added to the reaction solution to carry out separation of layers, and the water layer was extracted with ethyl acetate. The organic layers were combined, washed with saturated sodium bicarbonate aqueous solution and saturated brine in that order and then dried using anhydrous sodium sulfate. The solvent was evaporated under a reduced pressure and the resulting residue was purified by a silica gel column chromatography (developing solvent; hexane:ethyl acetate=1:1 (v/v)) to obtain 410 mg of the title compound.

$^1$H-NMR (400 MHz, CDCl$_3$, TMS) δ: 1.26 (3 H, s), 1.43 (9 H, s), 1.50 (3 H, s), 1.60–1.91 (3 H, m), 1.64 (3 H, s), 1.74 (3 H, s), 1.91 (1 H, s), 2.04–2.16 (2 H, m), 2.32–2.37 (1 H, m), 2.34 (3 H, s), 2.93 (1 H, d, J=5.3 Hz), 3.85 (3 H, s), 4.18 (1 H, d, J=7.3 Hz), 4.22 (1 H, d, J=8.3 Hz), 4.33 (1 H, d, J=8.3 Hz), 4.79 (1 H, br s), 4.85 (1 H, br s), 4.92 (1 H, br s), 5.23 (1 H, d, J=5.8 Hz), 5.29–5.30 (2 H, m), 5.46 (1 H, d, J=10.3 Hz), 5.58 (1 H, d, J=17.1 Hz), 5.90 (1 H, d, J=9.7 Hz), 5.96–6.03 (2 H, m), 6.09 (1 H, t-like, J=8.4 Hz), 7.22 (1 H, dd, J=2.4, 8.8 Hz), 7.34 (1 H, d, J=8.8 Hz), 7.47 (2 H, t, J=7.8 Hz), 7.60 (1 H, t, J=7.8 Hz), 8.13 (2 H, d, J=7.8 Hz), 8.22 (1 H, d, J=2.4 Hz).

Step 3: (1S,2S,3R,4S,5R,8R,9S,10R,13S)-4-Acetoxy-2-benzoyloxy-5,20-epoxy-1-hydroxy-9,10-[(1S)-2-(morpholino)ethylidenedioxy]tax-11-en-13-yl (2R,3S)-3-(tert-butoxycarbonylamino)-2-hydroxy-3-(5-methoxy-2-pyridyl)propionate A 400 mg portion of the compound obtained in the above step 2 was dissolved in 5 ml of tetrahydrofuran, and the solution was mixed with 5 ml of acetone, 5 ml of water, 5.9 mg of osmium tetroxide and 270 mg of N-methylmorpholine-N-oxide and stirred at room temperature for 4.5 hours. Ethyl acetate and 10% sodium thiosulfate aqueous solution were added to the reaction solution to carry out separation of layers, and the water layer was extracted with ethyl acetate. The organic layers were combined, washed with saturated sodium bicarbonate aqueous solution and saturated brine in that order and then dried with anhydrous sodium sulfate. The solvent was evaporated under a reduced pressure, the resulting residue was dissolved in 5 ml of tetrahydrofuran and then the solution was mixed with 5 ml of methanol, 5 ml of water and 990 mg of sodium metaperiodate and stirred at room temperature for 1.5 hours. Ethyl acetate and water were added to the reaction solution to carry out separation of layers, and the water-layer was extracted with ethyl acetate. The organic layers were combined, washed with saturated brine and then dried with anhydrous sodium sulfate. The solvent was evaporated under a reduced pressure, the resulting residue was dissolved in 30 ml of ethanol and then the solution was mixed with 0.2 ml of morpholine, 0.13 ml of acetic acid and 140 mg of sodium cyanoborohydride and stirred at room temperature for 1 hour. Saturated sodium bicarbonate aqueous solution, ethyl acetate and water were added to the reaction solution to carry out separation of layers, and the water layer was extracted with ethyl acetate. The organic layers were combined, washed with saturated brine and then dried with anhydrous sodium sulfate. The solvent was evaporated under a reduced pressure and the resulting residue was purified by a silica gel column chromatography (developing solvent; chloroform:methanol=50:1 (v/v)) to obtain 220 mg of the title compound.

Melting point: 160–161° C.

$^1$H-NMR (400 MHz, CDCl$_3$, TMS) δ: 1.27 (3 H, s), 1.43 (9 H, s), 1.48 (3 H, s), 1.60 (3 H, s), 1.72 (3 H, s), 1.78–2.12 (6 H, m), 2.31–2.38 (1 H, m), 2.34 (3 H, s), 2.58–2.68 (4 H, m), 2.71 (1 H, dd, J=5.4, 13.2 Hz), 2 79 (1 H, dd, J=3.9, 13.2 Hz), 2.93 (1 H, d, J=5.3 Hz), 3.75 (4 H, t, J=4.9 Hz), 3.86 (3 H, s), 4.12 (1 H, d, J=7.3 Hz), 4.21 (1 H, d, J=8.3 Hz), 4.33 (1 H, d, J=8.3 Hz), 4.76 (1 H, br s), 4.85 (1 H, br s), 4.92 (1 H, s), 5.04 (1 H, t, J=4.6 Hz), 5.23 (1 H, d, J=6.9 Hz), 5.29 (1 H, d, J=8.8 Hz), 5.90 (1 H, d, J=9.3 Hz), 5.98 (1 H, d, J=4.9 Hz), 6.08 (1 H, t-like, J=8.3 Hz), 7.22 (1 H, dd, J=2.9, 8.8 Hz), 7.34 (1 H, d, J=8.8 Hz), 7.47 (2 H, t, J=7.8 Hz), 7.60 (1 H, t, J=7.8 Hz), 8.13 (2 H, d, J=7.8 Hz), 8.22 (1 H, d, J=2.9 Hz).

Elemental analysis (for $C_{49}H_{65}N_3O_{15}$)
Calcd.: C, 62.87; H, 7.00; N, 4.49
Found: C, 62.66; H, 7.08; N, 4.28.

EXAMPLE 2

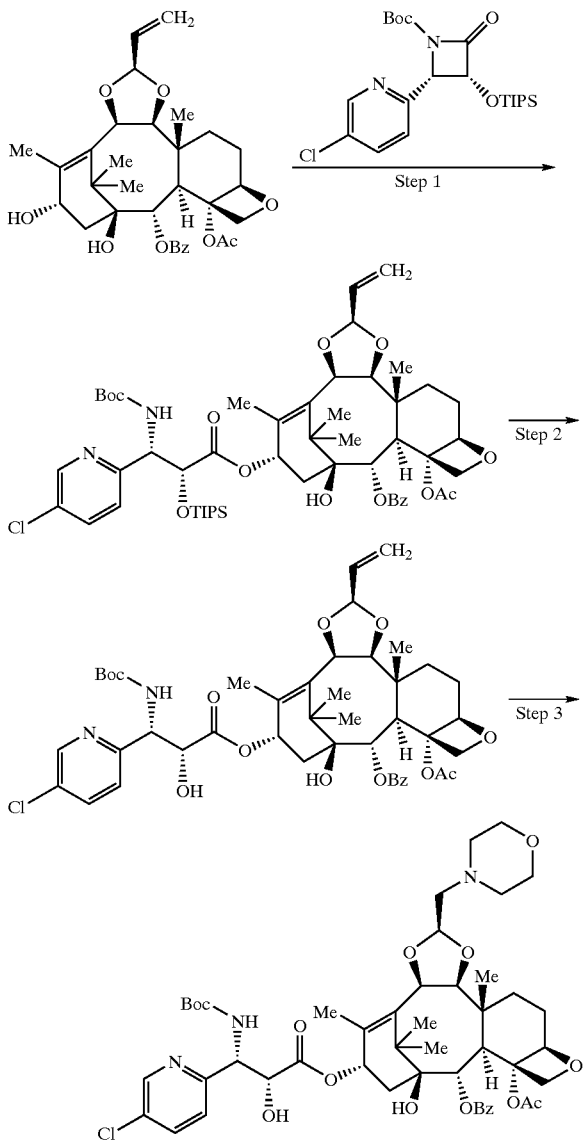

Step 1: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-3-(5-chloro-2-pyridyl)-2-triisopropylsilyloxypropionate The title compound was obtained by repeating the same procedure of the step 1 of Example 1, except that (3R,4S)-1-(tert-butoxycarbonyl)-4-(5-chloro-2-pyridyl)-3-triisopropylsilyloxy-2-azetidinone was used instead of (3R,4S)-1-(tert-butoxycarbonyl)-4-(5-methoxy-2-pyridyl)-3-triisopropylsilyloxy-2-azetidinone.

$^1$H-NMR (400 MHz, CDCl$_3$, TMS) δ: 0.87–0.94 (21 H, m), 1.18–1.69 (2 H, m), 1.31 (3 H, s), 1.41 (9 H, s), 1.52 (3 H, s), 1.65 (3 H, s), 1.82 (3 H, s), 1.72–2.05 (2 H, m), 2.24–2.34 (2 H, m), 2.48 (3 H, s), 2.97 (1 H, d, J=5.4 Hz), 4.19–4.23 (2 H, m), 4.33 (1 H, d, J=7.8 Hz), 4.95 (1 H, s), 5.21 (1 H, d, J=5.8 Hz), 5.27–5.31 (2 H, m), 5.42–5.47 (3 H, m), 5.58 (1 H, d, J=17.5 Hz), 5.96–6.04 (2 H, m), 6.11 (1 H, t, J=8.8 Hz), 7.38 (1 H, d, J=8.3 Hz), 7.44 (2 H, t, J=7.3 Hz), 7.57 (1 H, t, J=7.3 Hz), 7.65 (1 H, dd, J=8.3 Hz, 2.5 Hz), 8.13 (2 H, d, J=7.3 Hz), 8.53 (1 H, d, J=2.5 Hz).

Step 2: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-3-(5-chloro-2-pyridyl)-2-hydroxypropionate The title compound was obtained by carrying out the same procedure of the step 2 of Example 1, except that the compound obtained in the above step 1 was used as the material.

$^1$H-NMR (400 MHz, CDCl$_3$, TMS) δ: 1.26 (3 H, s), 1.22–1.65 (2 H, m), 1.43 (9 H, s), 1.49 (3 H, s), 1.64 (3 H, s), 1.74 (3 H, s), 1.75–2.09 (2 H, m), 2.30–2.39 (2 H, m), 2.33 (3 H, s), 2.94 (1 H, d, J=4.9 Hz), 4.18 (1 H, d, J=5.3 Hz), 4.22 (1 H, d, J=8.3 Hz), 4.32 (1 H, d, J=8.3 Hz), 4.61 (1 H, br s), 4.92 (2 H, m), 5.24 (1 H, d, J=6.3 Hz), 5.30 (1 H, d, J=6.8 Hz), 5.36 (1 H, d, J=9.3 Hz), 5.46 (1 H, d, J=10.5 Hz), 5.58 (1 H, d, J=17.5 Hz), 5.87 (1 H, d, J=9.3 Hz), 5.96–6.05 (2 H, m), 6.11 (1 H, t, J=7.8 Hz), 7.39 (1 H, d, J=8.3 Hz), 7.47 (2 H, t, J=7.3 Hz), 7.60 (1 H, t, J=7.3 Hz), 7.69 (1 H, dd, J=8.3 Hz, 2.4 Hz), 8.12 (2 H, d, J=7.3 Hz), 8.51 (1 H, d, J=2.4 Hz).

Step 3: (1S,2S,3R,4S,5R,8R,9S,10R,13S)-4-Acetoxy-2-benzoyloxy-5,20-epoxy-1-hydroxy-9,10-[(1S)-2-(morpholino)ethylidenedioxy]tax-11-en-13-yl (2R,3S)-3-(tert-butoxycarbonylamino)-3-(5-chloro-2-pyridyl)-2-hydroxypropionate The title compound was obtained by carrying out the same procedure of the step 3 of Example 1, except that compound obtained in the above step 2 was used as the material.

Melting point: 146–150° C.

$^1$H-NMR (400 MHz, CDCl$_3$, TMS) δ: 1.26 (3 H, s), 1.20–1.72 (2 H, m), 1.43 (9 H, s), 1.48 (3 H, s), 1.63 (3 H, s), 1.73 (3 H, s), 1.75–2.03 (2 H, m), 2.33 (3 H, s), 2.30–2.38 (2 H, m), 2.59–2.69 (4 H, m), 2.72 (1 H, dd, J=5.4, 13.2 Hz), 2.79 (1 H, dd, J=3.9, 13.2 Hz), 2.92 (1 H, d, J=4.9 Hz), 3.74 (4 H, t, J=4.9 Hz), 4.12 (1 H, d, J=7.9 Hz), 4.22 (1 H, d, J=8.8 Hz), 4.32 (1 H, d, J=8.8 Hz), 4.59 (1 H, br s), 4.91 (2 H, m), 5.05 (1 H, t, J=4.4 Hz), 5.24 (1 H, d, J=6.8 Hz), 5.35 (1 H, d, J=9.3 Hz), 5.87 (1 H, d, J=9.8 Hz), 5.99 (1 H, d, J=4.9 Hz), 6.10 (1 H, t, J=8.0 Hz), 7.39 (1 H, d, J=8.3 Hz), 7.47 (2 H, t, J=7.3 Hz), 7.60 (1 H, t, J=7.3 Hz), 7.69 (1 H, dd, J=8.3 Hz, 2.4 Hz), 8.12 (2 H, d, J=7.3 Hz), 8.50 (1 H, d, J=2.5 Hz).

Elemental analysis (for $C_{48}H_{62}ClN_3O_{14} \cdot H_2O$)
Calcd.: C, 60.15; H, 6.73; N, 4.38; Cl, 3.70
Found: C, 60.15; H, 6.74; N, 4.20; Cl, 3.63.

EXAMPLE 3

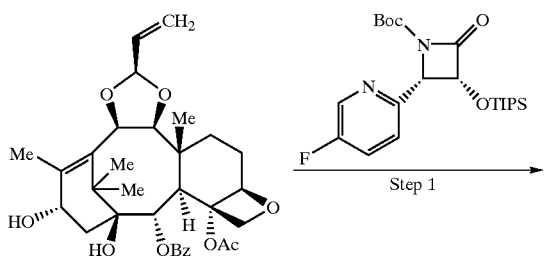

-continued

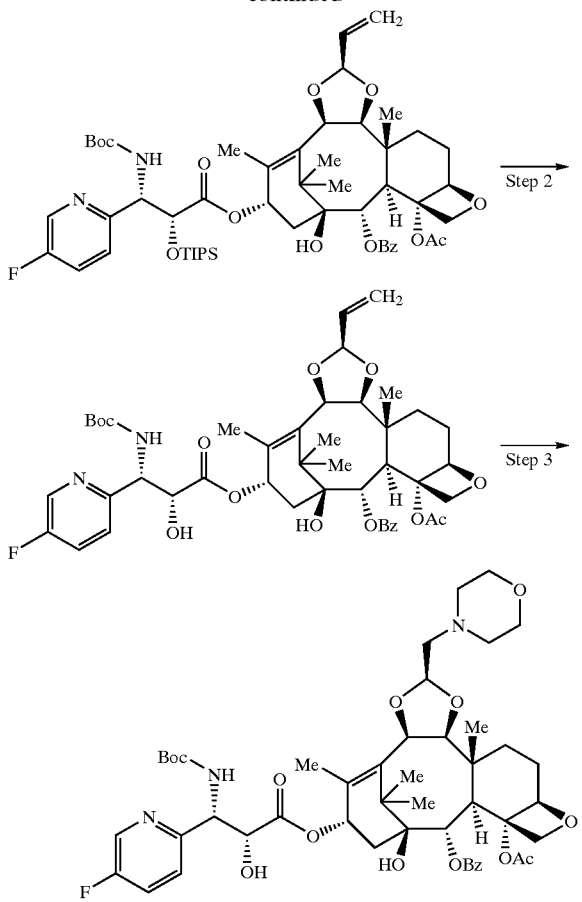

Step 1: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-3-(5-fluoro-2-pyridyl)-2-triisopropylsilyloxypropionate The title compound was obtained by carrying out the same procedure of the step 1 of Example 1, except that (3R,4S)-1-(tert-butoxycarbonyl)-4-(5-fluoro-2-pyridyl)-3-triisopropylsilyloxy-2-azetidinone was used instead of (3R,4S)-1-(tert-butoxycarbonyl)-4-(5-methoxy-2-pyridyl)-3-triisopropylsilyloxy-2-azetidinone.

$^1$H-NMR (400 MHz, CDCl$_3$, TMS) δ: 0.87–0.94 (21 H, m), 1.20–1.70 (2 H, m), 1.31 (3 H, s), 1.41 (9 H, s), 1.52 (3 H, s), 1.65 (3 H, s), 1.82 (3 H, s), 1.75–2.07 (2 H, m), 2.26–2.32 (2 H, m), 2.49 (3 H, s), 2.97 (1 H, d, J=5.4 Hz), 4.19–4.23 (2 H, m), 4.33 (1 H, d, J=8 Hz), 4.96 (1 H, s), 5.21 (1 H, d, J=5.9 Hz), 5.27–5.32 (2 H, m), 5.43–5.49 (3 H, m), 5.58 (1 H, d, J=17.5 Hz), 5.96–6.04 (2 H, m), 6.12 (1 H, t, J=8 Hz), 7.36–7.47 (4 H, m), 7.57 (1 H, t, J=7.3 Hz), 8.13 (2 H, d, J=7.3 Hz), 8.43 (1 H, d, J=2.4 Hz).

Step 2: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-3-(5-fluoro-2-pyridyl)-2-hydroxypropionate The title compound was obtained by carrying out the same procedure of the step 2 of Example 1, except that the compound obtained in the above step 1 was used as the material.

$^1$H-NMR (400 MHz, CDCl$_3$, TMS) δ: 1.27 (3 H, s), 1.20–1.68 (2 H, m), 1.44 (9 H, s), 1.49 (3 H, s), 1.64 (3 H, s), 1.74 (3 H, s), 1.75–2.05 (2 H, m), 2.30–2.39 (2 H, m), 2.34 (3 H, s), 2.93 (1 H, d, J=4.9 Hz), 4.18 (1 H, d, J=6.8 Hz), 4.23 (1 H, d, J=8.3 Hz), 4.33 (1 H, d, J=8.3 Hz), 4.62 (1 H, d, J=2.5 Hz), 4.90–4.92 (2 H, m), 5.24 (1 H, d, J=5.8 Hz), 5.30 (1 H, d, J=6.8 Hz), 5.37 (1 H, d, J=9.3 Hz), 5.46 (1 H, d, J=10.2 Hz), 5.58 (1 H, d, J=17 Hz), 5.90 (1 H, d, J=10.2 Hz), 5.96–6.05 (2 H, m), 6.10 (1 H, t, J=7.8 Hz), 7.40–7.49 (4 H, m), 7.60 (1 H, t, J=7.3 Hz), 8.12 (2 H, d, J=7.3 Hz), 8.41 (1 H, s).

Step 3: (1S,2S,3R,4S,5R,8R,9S,10R,13S)-4-Acetoxy-2-benzoyloxy-5,20-epoxy-1-hydroxy-9,10-[(1S)-2-(morpholino)ethylidenedioxy]tax-11-en-13-yl (2R,3S)-3-(tert-butoxycarbonylamino)-3-(5-fluoro-2-pyridyl)-2-hydroxypropionate The title compound was obtained by carrying out the same procedure of the step 3 of Example 1, except that the compound obtained in the above step 2 was used as the material.

Melting point: 148–152° C.

$^1$H-NMR (400 MHz, CDCl$_3$, TMS) δ: 1.26 (3 H, s), 1.20–1.69 (2 H, m), 1.43 (9 H, s), 1.48 (3 H, s), 1.62 (3 H, s), 1.72 (3 H, s), 1.75–2.02 (2 H, m), 2.33 (3 H, s), 2.30–2.39 (2 H, m), 2.59–2.69 (4 H, m), 2.71 (1 H, dd, J=5.4, 13.2 Hz), 2.79 (1 H, dd, J=3.9, 13.2 Hz), 2.92 (1 H, d, J=4.9 Hz), 3.74 (4 H, t, J=4.9 Hz), 4.12 (1 H, d, J=7.3 Hz), 4.22 (1 H, d, J=8.3 Hz), 4.32 (1 H, d, J=8.3 Hz), 4.60 (1 H, br s), 4.90–4.92 (2 H, m), 5.04 (1 H, t, J=4.9 Hz), 5.24 (1 H, d, J=6.8 Hz), 5.36 (1 H, d, J=9.3 Hz), 5.89 (1 H, d, J=9.8 Hz), 5.99 (1 H, d, J=4.9 Hz), 6.09 (1 H, t, J=8.0 Hz), 7.42–7.49 (3 H, m), 7.60 (1 H, t, J=7.3 Hz), 7.60 (1 H, t, J=7.3 Hz), 8.12 (2 H, d, J=7.3 Hz), 8.40 (1 H, s).

Elemental analysis (for C$_{48}$H$_{62}$FN$_3$O$_{14}$.H$_2$O)
Calcd.: C, 61.19; H, 6.85; N, 4.46; F, 2.02
Found: C, 61.16; H, 6.85; N, 4.36; F, 2.05.

EXAMPLE 4

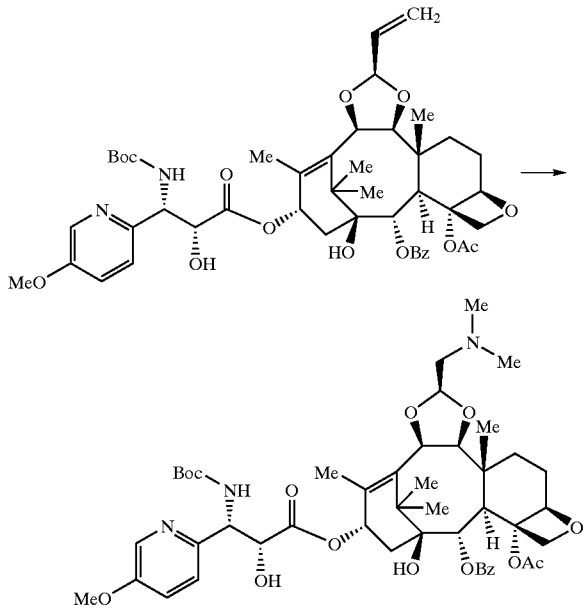

(1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-2-hydroxy-3-(5-methoxy-2-pyridyl)propionate The title compound was obtained by carrying out the same procedure of the step 3 of Example 1, except that the compound obtained in the step 2 of Example 1 was used as the material, and dimethylamine (2 M methanol solution) was used instead of morpholine.

¹H-NMR (400 MHz, CDCl₃, TMS) δ: 1.26 (3 H, s), 1.43 (9 H, s), 1.48 (3 H, s), 1.61 (3 H, s), 1.73 (3 H, s), 1.83–1.97 (3 H, m), 2.04–2.12 (2 H, m), 2.31–2.38 (2 H, m), 2.34 (3 H, s), 2.38 (6 H, s), 2.64–2.76 (2 H, m), 2.93 (1 H, d, J=4.9 Hz), 3.85 (3 H, s), 4.13 (1 H, d, J=7.4 Hz), 4.21 (1 H, d, J=8.3 Hz), 4.33 (1 H, d, J=8.3 Hz), 4.84 (1 H, d, J=2.4 Hz), 4.92 (1 H, s), 5.01 (1 H, t, J=4.9 Hz), 5.24 (1 H, d, J=6.8 Hz), 5.29 (1 H, d, J=8.8 Hz), 5.91 (1 H, d, J=9.3 Hz), 5.99 (1 H, d, J=5.4 Hz), 6.08 (1 H, t, J=7.8 Hz), 7.23 (1 H, dd, J=3.0, 8.3 Hz), 7.34 (1 H, d, J=8.8 Hz), 7.47 (2 H, t, J=7.8 Hz), 7.60 (1 H, t, J=7.8 Hz), 8.12 (2 H, d, J=7.8 Hz), 8.22 (1 H, d, J=3.0 Hz).

EXAMPLE 5

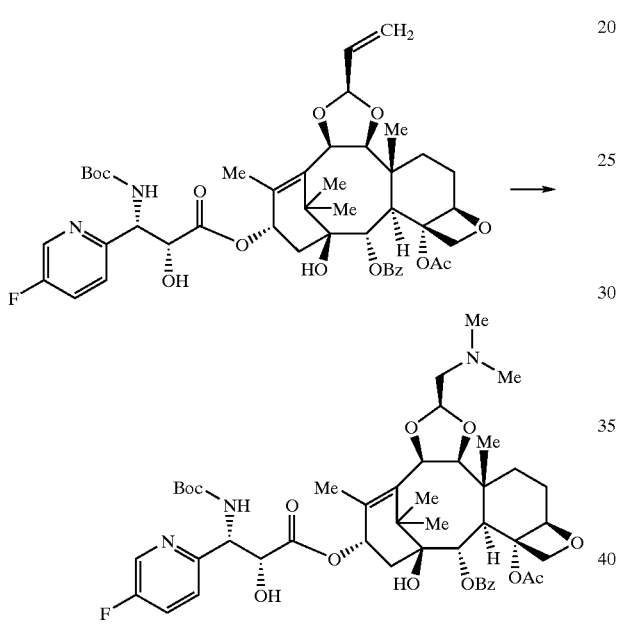

(1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butyoxycarbonylamino)-3-(5-fluoro-2-pyridyl)-2-hydroxypropionate The title compound was obtained by carrying out the same procedure of the step 3 of Example 1, except that the compound obtained in the step 2 of Example 3 was used as the material, and dimethylamine (2 M methanol solution) was used instead of morpholine.

¹H-NMR (400 MHz, CDCl₃, TMS) δ: 1.26 (3 H, s), 1.20–1.70 (2 H, m), 1.43 (9 H, s), 1.48 (3 H, s), 1.62 (3 H, s), 1.73 (3 H, s), 1.75–2.01 (3 H, m), 2.33 (3 H, s), 2.38 (6 H, s), 2.32–2.39 (2 H, m), 2.66 (1 H, dd, J=5.4, 13.2 Hz), 2.74 (1 H, dd, J=4.0, 13.2 Hz), 2.93 (1 H, d, J=4.9 Hz), 4.12 (1 H, d, J=7.3 Hz), 4.22 (1 H, d, J=8.3 Hz), 4.32 (1 H, d, J=8.3 Hz), 4.90–4.92 (2 H, m), 5.02 (1 H, t, J=5.4 Hz), 5.25 (1 H, d, J=6.8 Hz), 5.36 (1 H, d, J=6.8 Hz), 5.90 (1 H, d, J=8.8 Hz), 5.99 (1 H, d, J=4.9 Hz), 6.09 (1 H, t, J=8.1 Hz), 7.42–7.49 (4 H, m), 7.60 (1 H, t, J=7.3 Hz), 8.12 (2 H, d, J=7.3 Hz), 8.41 (1 H, s).

EXAMPLE 6

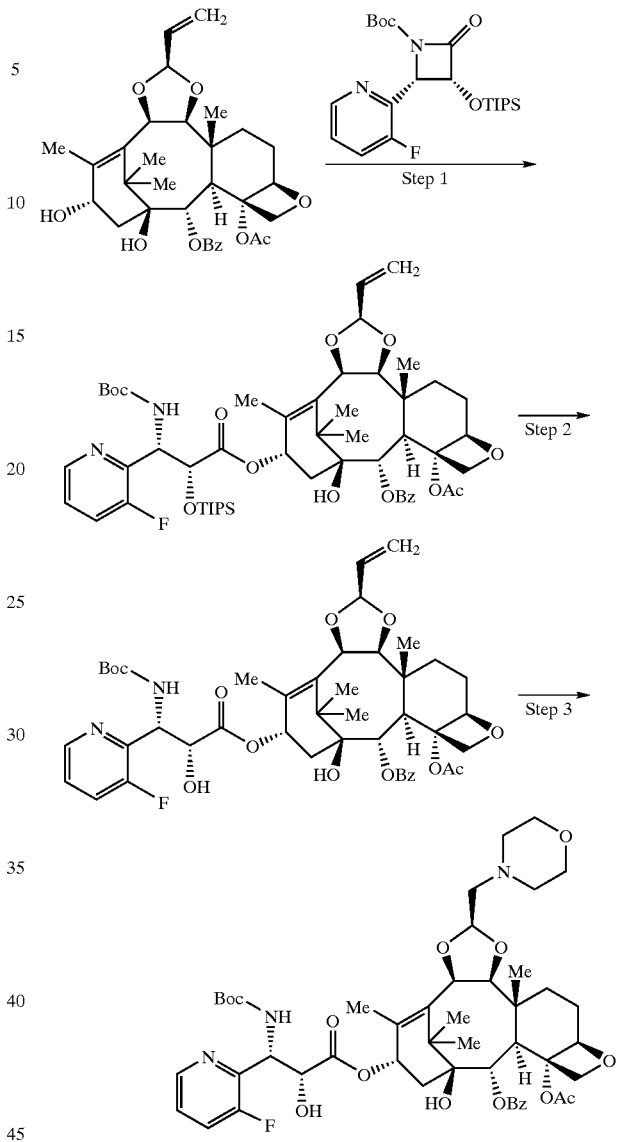

Step 1: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-3-(3-fluoro-2-pyridyl)-2-triisopropylsilyloxypropionate The title compound was obtained by carrying out the same procedure of the step 1 of Example 1, except that (3R,4S)-1-(tert-butoxycarbonyl)-4-(3-fluoro-2-pyridyl)-3-triisopropylsilyloxy-2-azetidinone was used instead of (3R,4S)-1-(tert-butoxycarbonyl)-4-(5-methoxy-2-pyridyl)-3-triisopropylsilyloxy-2-azetidinone.

¹H-NMR (400 MHz, CDCl₃, TMS) δ: 0.89–0.93 (21 H, m), 1.28 (3 H, s), 1.39 (9 H, s), 1.54 (3 H, s), 1.66 (3 H, s), 1.82 (3 H, s), 1.61–1.64 (3 H, m), 1.89–1.96 (2 H, m), 2.33–2.39 (2 H, m), 2.49 (3 H, s), 2.98 (1 H, d, J=4.8 Hz), 4.21–4.23 (2 H, m), 4.36 (1 H, d, J=7.8 Hz), 4.96 (2 H, br s), 5.20 (1 H, d, J=5.9 Hz), 5.27 (1 H, d, J=6.8 Hz), 5.46 (1 H, d, J=9.8 Hz), 5.58 (1 H, d, J=17.1 Hz), 5.61 (1 H, d, J=6.8 Hz), 5.96–6.03 (2 H, m), 6.08–6.12 (2 H, m), 7.25–7.29 (1 H, m), 7.40 (1 H, t, J=8.3 Hz), 7.47 (1 H, t, J=7.8 Hz), 7.59 (1 H, t, J=7.8 Hz), 8.16 (2 H, d, J=7.8 Hz), 8.39 (1 H, d, J=3.4 Hz).

Step 2: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-3-(3-fluoro-2-pyridyl)-2-hydroxypropionate The title compound was obtained by carrying out the same procedure of the step 2 of Example 1, except that the compound obtained in the above step 1 was used as the material.

$^1$H-NMR (400 MHz, CDCl$_3$, TMS) δ: 1.30 (3 H, s), 1.41 (9 H, s), 1.51 (3 H, s), 1.65 (3 H, s), 1.81 (3 H, s), 1.57–1.63 (3 H, m), 1.89–1.95 (2 H, m), 2.03–2.10 (1 H, m), 2.35 (3 H, s), 2.43–2.49 (1 H, m), 2.95 (1 H, d, J=4.9 Hz), 4.20 (1 H, d, J=7.4 Hz), 4.23 (1 H, d, J=8.8 Hz), 4.33 (1 H, d, J=8.3 Hz), 4.68 (1 H, d, J=2.5 Hz), 4.92 (1 H, s), 5.24 (1 H, d, J=6.4 Hz), 5.31 (1 H, d, J=6.8 Hz), 5.46 (1 H, d, J=9.8 Hz), 5.58 (1 H, d, J=17.1 Hz), 5.65 (1 H, d, J=18.3 Hz), 5.97–6.05 (2 H, m), 6.10 (1 H, t, J=8.8 Hz), 6.21 (1 H, d, J=8.3 Hz), 7.29–7.32 (1 H, m), 7.43–7.49 (3 H, m), 7.60 (1 H, t, J=7.3 Hz), 8.14 (2 H, d, J=7.3 Hz), 8.41 (1 H, d, J=4.9 Hz).

Step 3: (1S,2S,3R,4S,5R,8R,9S,10R,13S)-4-Acetoxy-2-benzoyloxy-5,20-epoxy-1-hydroxy-9,10-[(1S)-2-(morpholino)ethylidenedioxy]tax-11-en-13-yl (2R,3S)-3-(tert-butoxycarbonylamino)-3-(3-fluoro-2-pyridyl)-2-hydroxypropionate The title compound was obtained by carrying out the same procedure of the step 3 of Example 1, except that the compound obtained in the above step 2 was used as the material.

$^1$H-NMR (400 MHz, CDCl$_3$, TMS) δ: 1.29 (3 H, s), 1.40 (9 H, s), 1.49 (3 H, s), 1.61 (3 H, s), 1.79 (3 H, s), 1.70–2.03 (5 H, m), 2.30–2.44 (2 H, m), 2.35 (3 H, s), 2.61–2.65 (4 H, m), 2.70–2.82 (2 H, m), 2.94 (1 H, d, J=4.8 Hz), 3.75 (4 H, t, J=4.9 Hz), 4.14 (1 H, d, J=7.3 Hz), 4.23 (1 H, d, J=8.3 Hz), 4.33 (1 H, d, J=7.8 Hz), 4.67 (1 H, s), 4.92 (1 H, s), 5.05 (1 H, t, J=4.9 Hz), 5.25 (1 H, d, J=7.3 Hz), 5.65 (1 H, d, J=7.8 Hz), 5.99 (1 H, d, J=5.4 Hz), 6.09 (1 H, t, J=7.8 Hz), 6.20 (1 H, d, J=8.3 Hz), 7.29–7.33 (1 H, m), 7.43–7.49 (3 H, m), 7.60 (1 H, t, J=7.3 Hz), 8.13 (2 H, d, J=7.3 Hz), 8.40 (1 H, d, J=4.9 Hz).

EXAMPLE 7

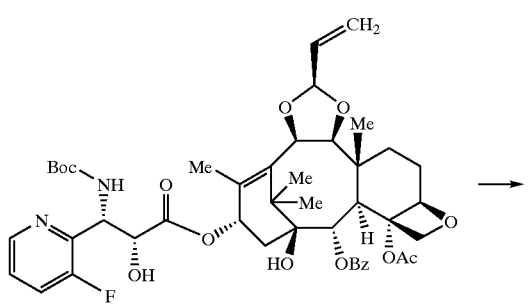

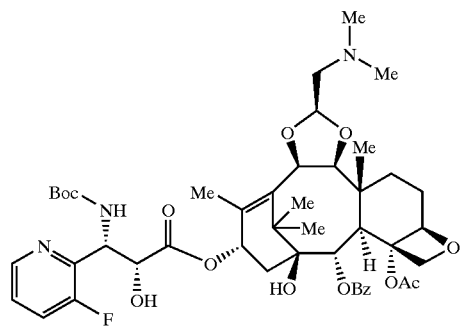

(1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate The title compound was obtained by carrying out the same procedure of the step 3 of Example 1, except that the compound obtained in the step 2 of Example 6 was used as the material, and dimethylamine (2 M methanol solution) was used instead of morpholine.

$^1$H-NMR (400 MHz, CDCl$_3$, TMS) δ: 1.29 (3 H, s), 1.41 (9 H, s), 1.49 (3 H, s), 1.63 (3 H, s), 1.79 (3 H, s), 1.86–2.08 (5 H, m), 2.32–2.38 (2 H, m), 2.34 (3 H, s), 2.38 (6 H, s), 2.66 (1 H, dd, J=5.4, 13.6 Hz), 2.75 (1 H, dd, J=3.9, 13.6 Hz), 2.94 (1 H, d, J=4.9 Hz), 4.14 (1 H, d, J=6.9 Hz), 4.23 (1 H, d, J=8.3 Hz), 4.33 (1 H, d, J=8.3 Hz), 4.68 (1 H, d, J=2.9 Hz), 4.92 (1 H, s), 5.02 (1 H, t, J=4.9 Hz), 5.25 (1 H, d, J=6.8 Hz), 5.65 (1 H, d, J=8.3 Hz), 6.00 (1 H, d, J=4.9 Hz), 6.09 (1 H, t, J=7.8 Hz), 6.21 (1 H, d, J=8.3 Hz), 7.28–7.33 (1 H, m), 7.43–7.49 (3 H, m), 7.60 (1 H, t, J=7.3 Hz), 8.14 (2 H, d, J=7.3 Hz), 8.40 (1 H, d, J=4.4 Hz).

Referential Example

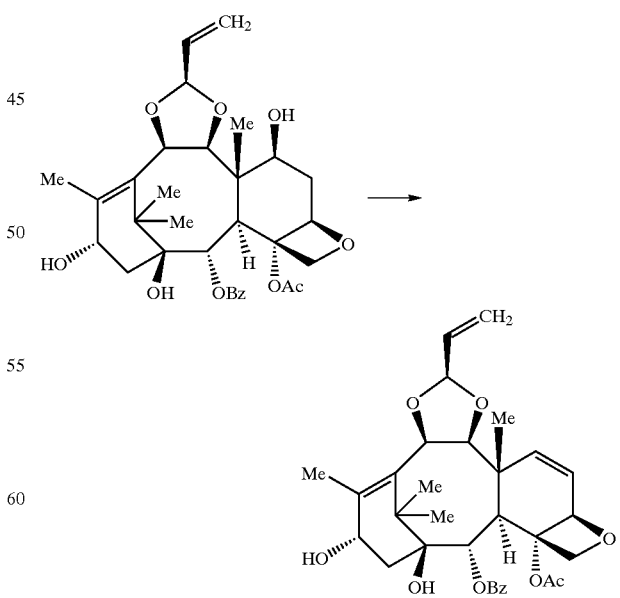

(1S,2S,3R,4S,5R,8R,9S,10R,13S)-4-Acetoxy-2-benzoyloxy-5,20-epoxy-1,13-dihydroxy-9,10-[(1S)-2-propenylidenedioxy]tax-6,11-diene In 360 ml of methylene chloride were dissolved 18 g of (1S,2S,3R,4S,5R,7S,8S,9S,10R,13S)-4-acetoxy-2-benzoyloxy-5,20-epoxy-9,10-[(1R)-2-propenylidenedioxy]-1,7,13-trihydroxytax-11-ene and 37.7 g of 4-dimethylaminopyridine. Under ice cooling, 20.7 ml of trifluoromethanesulfonic anhydride was added and the mixture was stirred for 1.5 hours at the same temperature. The reaction mixture was poured into a mixture of ethyl acetate and a saturated aqueous solution of sodium bicarbonate to separate the mixture into two layers. The water layer was extracted with ethyl acetate. After the extract and the organic layer were combined, the mixture was washed with water and saturated brine, and dried over anhydrous sodium sulfate. The solvent was evaporated under a reduced pressure and the resulting residue was purified by a silica gel column chromatography (eluted with chloroform:acetone=50:1 (v/v)) to obtain 11.5 g of the title compound as a white substance.

$^1$H-NMR (400 MHz, CDCl$_3$, TMS) d: 1.15 (3H, s), 1.52 (3H, s), 1.56 (3H, s), 1.77 (1H, s), 1.90 (3H, s), 2.07 (1H, dd, J=6.8, 15.1 Hz), 2.23 (1H, d, J=9.3 Hz), 2.36 (3H, s), 3.21 (1H, d, J=5.9 Hz), 4.00 (1H, d, J=7.4 Hz), 4.30 (2H, ABq, J=7.8 Hz), 4.79–4.83 (2H, m), 5.25–5.27 (2H, m), 5.48 (1H, d, J=10.3 Hz), 5.60 (1H, d, J=17.1 Hz), 5.70 (1H, dd, J=3.9, 10.2 Hz), 5.96 (1H, d, J=5.9 Hz), 5.98–6.07 (1H,m), 6.13 (1H, d, J=10.2 Hz), 7.49 (2H, t, J=7.3 Hz), 7.61 (1H, t, J=7.3 Hz), 8.16 (2H, d, J=7.3 Hz).

EXAMPLE 8

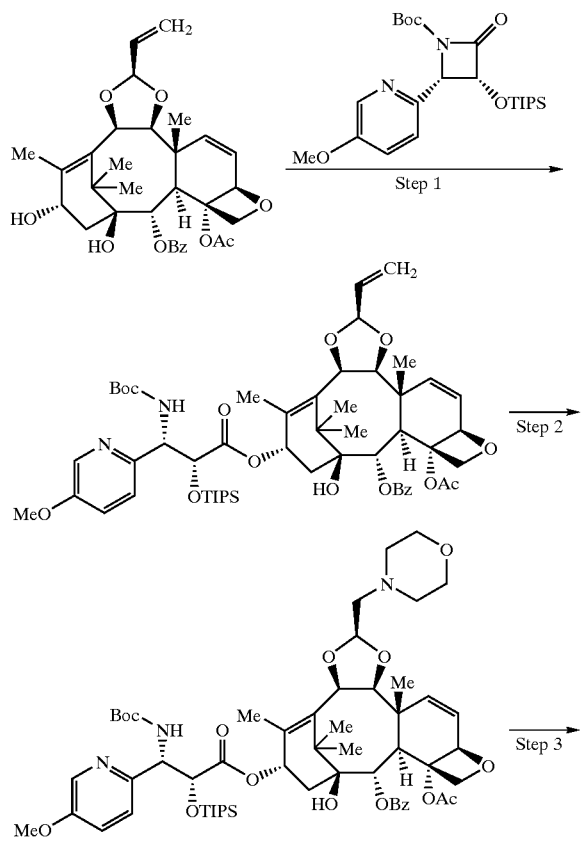

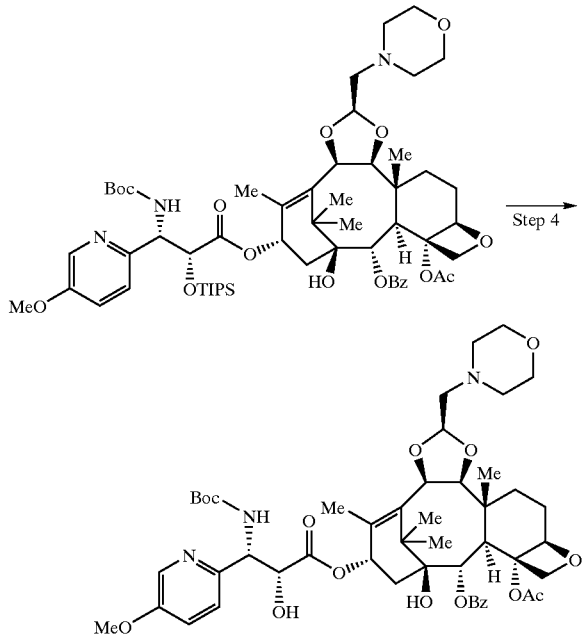

Step 1: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-6,11-dien-13-yl (2R,3S)-3-(tert-butoxycarbonylamino)-3-(5-methoxy-2-pyridyl)-2-triIsopropylsilyloxypropionate A 300 mg portion of (1S,2S,3R,4S,5R,8R,9S,10R,13S)-4-acetoxy-2-benzoyloxy-5,20-epoxy-1,13-dihydroxy-9,10-[(1S)-2-propenylidenedioxy]tax-6,11-diene was dissolved in 10 ml of dry tetrahydrofuran, and the solution was mixed with 0.63 ml of lithium hexamethyldisilazide (1 M tetrahydrofuran solution) at −60° C. and stirred for 20 minutes. A 5 ml portion of tetrahydrofuran solution containing 280 mg of (3R,4S)-1-(tert-butoxycarbonyl)-4-(5-methoxy-2-pyridyl)-3-triisopropylsilyloxy-2-azetidinone was added to the reaction solution at the same temperature, and the mixture was stirred under ice-cooling for 30 minutes. Saturated ammonium chloride aqueous solution and ethyl acetate were added to the reaction solution to carry out separation of layers, and the water layer was extracted with ethyl acetate. The organic layers were combined, washed with saturated brine and then dried with anhydrous sodium sulfate. The solvent was evaporated under a reduced pressure and the resulting residue was purified by a silica gel column chromatography (elution with hexane:ethyl acetate=5:1 (v/v)) to obtain 530 mg of the title compound.

$^1$H-NMR (400 MHz, CDCl$_3$, TMS) δ: 0.87–0.93 (21 H, m), 1.29 (3 H, s), 1.41 (9 H, s), 1.54 (3 H, s), 1.69 (3 H, s), 1.75 (3 H, s), 1.82 (1 H, s), 2.29 (1 H, dd, J=9.8, 15.1 Hz), 2.40 (1 H, dd, J=8.8, 15.1 Hz), 2.53 (3 H, s), 3.13 (1 H, d, J=5.8 Hz), 3.85 (3 H, s), 4.04 (1 H, d, J=7.3 Hz), 4.30 (2 H, br s), 4.90 (1 H, d, J=3.9 Hz), 5.20–5.23 (2 H, m), 5.28 (1 H, d, J=9.8 Hz), 5.38 (1 H, s), 5.47–5.49 (2 H, m), 5.60 (1 H, d, J=17.0 Hz), 5.71 (1 H, dd, J=4.4, 10.2 Hz), 5.96–6.06 (2 H, m), 6.09–6.14 (2 H, m), 7.16 (1 H, dd, J=2.9, 8.3 Hz), 7.31 (1 H, d, J=8.3 Hz), 7.47 (2 H, t, J=7.8 Hz), 7.58 (1 H, t, J=7.8 Hz), 8.14 (2 H, d, J=7.8 Hz), 8.26 (1 H, d, J=2.9 Hz).

Step 2: (1S,2S,3R,4S,5R,8R,9S,10R,13S)-4-Acetoxy-2-benzoyloxy-5,20-epoxy-1-hydroxy-9,10-[(1S)-2-(morpholino)ethylidenedioxy]tax-6,11-dien-13-yl (2R,3S)-3-(tert-butoxycarbonylamino)-3-(5-methoxy-2-pyridyl)-2-triisopropylsilyloxy propionate A 520 mg portion of the compound obtained in the above step 1 was dissolved in 5 ml of tetrahydrofuran, and the solution was mixed with 5 ml of acetone, 5 ml of water, 13 mg of osmium tetraoxide and 300 mg of N-methylmorpholine-N-oxide and stirred at room temperature for 7.5 hours. Ethyl acetate and 10% sodium thiosulfate aqueous solution were added to the reaction solution to carry out separation of layers, and the water layer was extracted with ethyl acetate. The organic layers were combined, washed with saturated sodium bicarbonate aqueous solution and saturated brine in that order and then dried with anhydrous sodium sulfate. The solvent was evaporated under a reduced pressure, the resulting residue was dissolved in 5 ml of tetrahydrofuran and then the solution was mixed with 5 ml of methanol, 5 ml of water and 1.1 g of sodium metaperiodate and stirred at room temperature for 1.5 hours. Ethyl acetate and water were added to the reaction solution to carry out separation of layers, and the water layer was extracted with ethyl acetate. The organic layers were combined, washed with saturated brine and then dried with anhydrous sodium sulfate. The solvent was evaporated under a reduced pressure, the resulting residue was dissolved in 30 ml of ethanol and then the solution was mixed under ice-cooling with 0.22 ml of morpholine, 0.15 ml of acetic acid and 160 mg of sodium cyanoborohydride and stirred at room temperature for 1 hour. Saturated sodium bicarbonate aqueous solution, ethyl acetate and water were added to the reaction solution to carry out separation of layers, and the water layer was extracted with ethyl acetate. The organic layers were combined, washed with saturated brine and then dried with anhydrous sodium sulfate. The solvent was evaporated under a reduced pressure and the resulting residue was purified by a silica gel column chromatography (elution with hexane:ethyl acetate=3:2 (v/v)) to obtain 290 mg of the title compound.

$^1$H-NMR (400 MHz, CDCl$_3$, TMS) δ: 0.87–0.93 (21 H, m), 1.28 (3 H, s), 1.41 (9 H, s), 1.53 (3 H, s), 1.55 (3 H, s), 1.73 (3 H, s), 1.80 (1 H, s), 2.26 (1 H, dd, J=8.8, 15.1 Hz), 2.39 (1 H, dd, J=9.8, 15.1 Hz), 2.53 (3 H, s), 2.60–2.68 (4 H, m), 2.74 (1 H, dd, J=4.9, 13.7 Hz), 2.81 (1 H, dd, J=4.9, 13.7 Hz), 3.12 (1 H, d, J=5.4 Hz), 3.76 (1 H, t, J=4.8 Hz), 3.85 (3 H, s), 3.99 (1 H, d, J=7.9 Hz), 4.30 (2 H, s), 4.89 (1 H, d, J=3.9 Hz), 5.02 (1 H, t, J=3.9 Hz), 5.14 (1 H, d, J=7.3 Hz), 5.27 (1 H, d, J=9.8 Hz), 5.37 (1 H, d, J=1.5 Hz), 5.47 (1 H, d, J=9.8 Hz), 5.69 (1 H, dd, J=3.9, 10.5 Hz), 5.94 (1 H, d, J=5.3 Hz), 6.07–6.13 (2 H, m), 7.16 (1 H, dd, J=2.9, 6.3 Hz), 7.30 (1 H, d, J=6.3 Hz), 7.47 (2 H, t, J=7.8 Hz), 7.58 (1 H, t, J=7.8 Hz), 8.15 (2 H, d, J=7.8 Hz), 8.26 (1 H, d, J=2.9 Hz).

Step 3: (1S,2S,3R,4S,5R,8R,9S,10R,13S)-4-Acetoxy-2-benzoyloxy-5,20-epoxy-1-hydroxy-9,10-[(1S)-2-(morpholino)ethylidenedioxy]tax-11-en-13-yl (2R,3S)-3-(tert-butoxycarbonylamino)-3-(5-methoxy-2-pyridyl)-2-triisopropylsilyloxypropionate A 235 mg portion of the compound obtained in the above step 2 was dissolved in 10 ml of ethanol, and the solution was mixed with 235 mg of 5% palladium-carbon catalyst (wet) and shaken for 10 hours under a hydrogen pressure (4 kg/cm$^2$=392 kPa). After removing the catalyst by filtration, the filtrate was concentrated to obtain 230 mg of the title compound.

$^1$H-NMR (400 MHz, CDCl$_3$, TMS) δ: 0.88–0.94 (21 H, m), 1.30 (3 H, s), 1.42 (9 H, s), 1.50 (3 H, s), 1.60 (3 H, s), 1.79 (3 H, s), 1.84–2.30 (7 H, m), 2.50 (3 H, s), 2.60–2.84 (4 H, m), 2.85–2.92 (2 H, m), 2.95 (1 H, d, J=4.4 Hz), 3.80 (4 H, t, J=4.4 Hz), 3.85 (3 H, s), 4.17 (1 H, d, J=7.3 Hz), 4.19 (1 H, d, J=8.7 Hz), 4.33 (1 H, d, J=8.3 Hz), 4.96 (1 H, s), 5.10 (1 H, br s), 5.22–5.28 (2 H, m), 5.40 (1 H, s), 5.48 (1 H, d, J=10.3 Hz), 5.96 (1 H, d, J=4.9 Hz), 6.10 (1 H, t, J=8.3 Hz), 7.12–7.17 (1 H, m), 7.31 (1 H, d, J=8.3 Hz), 7.45 (2 H, t, J=7.8 Hz), 7.57 (1 H, t, J=7.8 Hz), 8.13 (2 H, d, J=7.8 Hz), 8.26 (1 H, d, J=2.9 Hz).

Step 4: (1S,2S,3R,4S,5R,8R,9S,10R,13S)-4-Acetoxy-2-benzoyloxy-5,20-epoxy-1-hydroxy-9,10-[(1S)-2-(morpholino)ethylidenedioxy]tax-11-en-13-yl (2R,3S)-3-(tert-butoxycarbonylamino)-2-hydroxy-3-(5-methoxy-2-pyridyl)propionate A 230 mg portion of the compound obtained in the above step 3 was dissolved in 5 ml of dry tetrahydrofuran, 0.43 ml of tetrabutylammonium fluoride (1M tetrahydrofuran solution) was added to the solution under ice-cooling and then the mixture was stirred at the same temperature for 30 minutes. Saturated brine and ethyl acetate were added to the reaction solution to carry out separation of layers, and the water layer was extracted with ethyl acetate. The organic layers were combined, washed with saturated sodium bicarbonate aqueous solution and saturated brine in that order and then dried using anhydrous sodium sulfate. The solvent was evaporated under a reduced pressure and the resulting residue was purified by a silica gel column chromatography (elution with chloroform:methanol=50:1 (v/v)) and then recrystallized from aqueous ethanol to obtain 110 mg of the title compound. Its instrumental analysis data coincided with those of the compound obtained in the step 3 of Example 1.

EXAMPLE 9

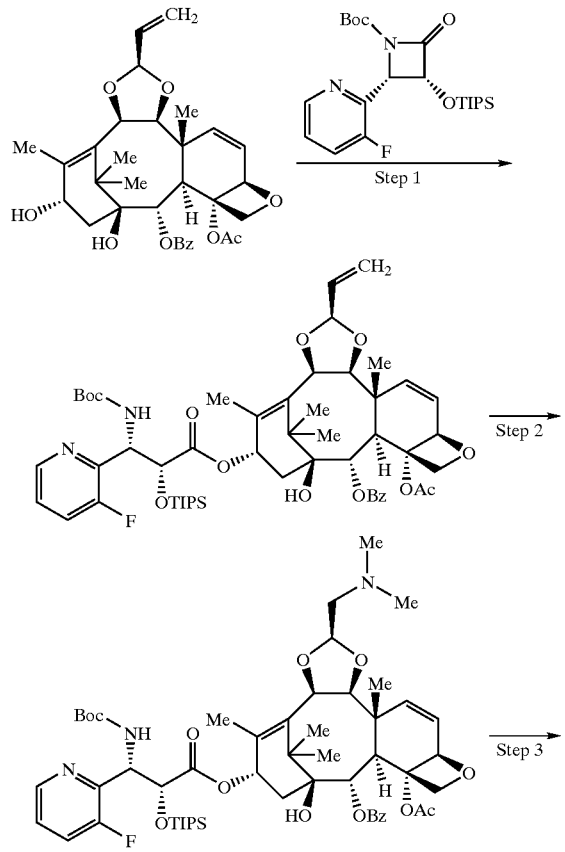

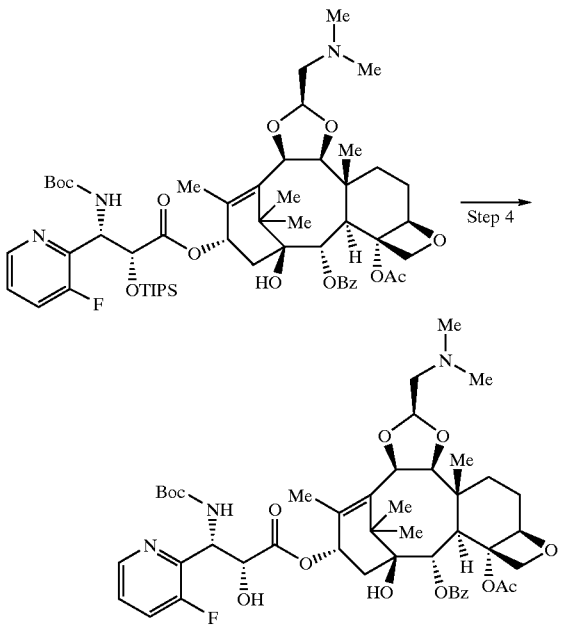

Step 1: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-6,11-dien-13-yl (2R,3S)-3-(tert-butoxycarbonylamino)-3-(3-fluoro-2-pyridyl)-2-triisopropylsilyloxypropionate The title compound was obtained by carrying out the same procedure of the step 1 of Example 8, except that (3R,4S)-1-(tert-butoxycarbonyl)-4-(3-fluoro-2-pyridyl)-3-triisopropylsilyloxy-2-azetidinone was used instead of (3R,4S)-1-(tert-butoxycarbonyl)-4-(5-methoxy-2-pyridyl)-3-triisopropylsilyloxy-2-azetidinone.

$^1$H-NMR (400 MHz, CDCl$_3$, TMS) δ: 0.88–0.92 (21 H, m), 1.33 (3 H, s), 1.38 (9 H, s), 1.56 (3 H, s), 1.76 (3 H, s), 2.41–2.45 (2 H, m), 2.51 (3 H, s), 3.14 (1 H, d, J=5.8 Hz), 4.06 (1 H, d, J=7.8 Hz), 4.33 (2 H, s), 4.90 (1 H, d, J=4.4 Hz), 4.94 (1 H, d, J=2.4 Hz), 5.19–5.22 (2 H, m), 5.48 (1 H, d, J=10.3 Hz), 5.58–5.64 (2 H, m), 5.70 (1 H, dd, J=10.3, 4.4 Hz), 5.96–6.14 (5 H, m), 7.26–7.30 (1 H, m), 7.41 (1 H, t, J=8.5 Hz), 7.49 (2 H, t, J=7.5 Hz), 7.59 (1 H, t, J=7.5 Hz), 8.17 (2 H, d, J=7.5 Hz), 8.40 (1 H, d, J=4.4 Hz).

Step 2: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-6,11-dien-13-yl (2R,3S)-3-(tert-butoxycarbonylamino)-3-(3-fluoro-2-pyridyl)-2-triisopropylsilyloxypropionate The title compound was obtained by carrying out the same procedure of the step 2 of Example 8, except that the compound obtained in the above step 1 was used as the material, and dimethylamine (2 M methanol solution) was used instead of morpholine.

$^1$H-NMR (400 MHz, CDCl$_3$, TMS) δ: 0.87–0.92 (21 H, m), 1.32 (3 H, s), 1.38 (9 H, s), 1.55 (3 H, s), 1.57 (3 H, s), 1.75 (3 H, s), 2.39 (6 H, s), 2.42–2.45 (2 H, m), 2.51 (3 H, s), 2.66 (1 H, dd, J=5.1, 13.2 Hz), 2.74 (1 H, dd, J=4.2, 13.2 Hz), 3.14 (1 H, d, J=5.8 Hz), 4.01 (1 H, d, J=7.9 Hz), 4.32 (2 H, s), 4.90–4.94 (2 H, m), 5.00 (1 H, t, J=4.9 Hz), 5.15 (1 H, d, J=7.9 Hz), 5.63 (1 H, d, J=9.8 Hz), 5.69 (1 H, dd, J=9.8, 4.4 Hz), 5.95 (1 H, d, J=5.8 Hz), 6.07–6.13 (3 H, m), 7.26–7.28 (1 H, m), 7.41 (1 H, t, J=9.2 Hz), 7.49 (2 H, t, J=7.5 Hz), 7.59 (1 H, t, J=7.5 Hz), 8.17 (2 H, d, J=7.5 Hz), 8.40 (1 H, d, J=4.4 Hz).

Step 3: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-triisopropylsilyloxypropionate The title compound was obtained by carrying out the same procedure of the step 3 of Example 8, except that the compound obtained in the above step 2 was used as the material.

$^1$H-NMR (400 MHz, CDCl$_3$, TMS) δ: 0.83–0.93 (21 H, m), 1.35 (3 H, s), 1.38 (9 H, s), 1.52 (3 H, s), 1.56–2.07 (5 H, m), 1.62 (3 H, s), 1.81 (3 H, s), 2.34–2.43 (2 H, m), 2.38 (6 H, s), 2.49 (3 H, s), 2.66 (1 H, dd, J=5.4, 13.2 Hz), 2.74 (1 H, dd, J=3.4, 13.2 Hz), 2.98 (1 H, d, J=5.4 Hz), 4.17 (1 H, d, J=7.3 Hz), 4.22 (1 H, d, J=7.8 Hz), 4.36 (1 H, d, J=8.3 Hz), 4.96 (2 H, s), 5.00 (1 H, t, J=4.8 Hz), 5.22 (1 H, d, J=7.3 Hz), 5.60 (1 H, d, J=8.8 Hz), 5.98 (1 H, d, J=4.9 Hz), 6.08–6.10 (2 H, m), 7.26–7.28 (1 H, m), 7.40 (1 H, t, J=9.2 Hz), 7.48 (2 H, t, J=7.5 Hz), 7.59 (1 H, t, J=7.5 Hz), 8.16 (2 H, d, J=7.5 Hz), 8.40 (1 H, d, J=3.9 Hz).

Step 4: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate The title compound was obtained by carrying out the same procedure of the step 4 of Example 8, except that the compound obtained in the above step 3 was used as the material and the recrystallization from aqueous ethanol was not carried out. Its instrumental analysis data coincided with those of the compound obtained in the step 3 of Example 7.

EXAMPLE 10

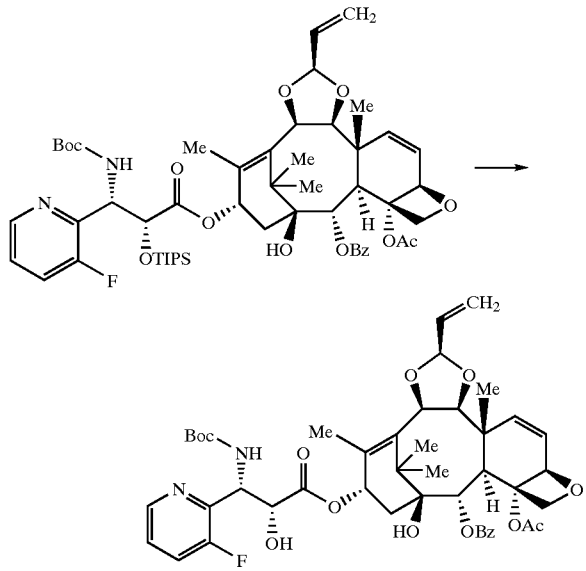

(1S,2S,3R,4S,5R,8R,9S,10R,13S)-4-Acetoxy-2-benzoyloxy-5,20-epoxy-1-hydroxy-9,10-[(1S)-2-propenylidenedioxy]tax-6,11-dien-13-yl (2R,3S)-3-(tert-butoxycarbonylamino)-3-(3-fluoro-2-pyridyl)-2-hydroxypropionate The title compound was obtained by carrying out the same procedure of the step 2 of Example 1, except that the compound obtained in the step 1 of Example 9 was used as the material.

¹H-NMR (400 MHz, CDCl₃, TMS) δ: 1.29 (3 H, s), 1.39 (9 H, s), 1.54 (3 H, s), 1.60 (3 H, s), 1.74 (3 H, s), 1.91 (1 H, s), 2.35–2.48 (2 H, m), 2.41 (3 H, s), 3.11 (1 H, d, J=5.4 Hz), 3.92 (1 H, br s), 4.03 (1 H, d, J=7.6 Hz), 4.27 (1 H, d, J=8.1 Hz), 4.33 (1 H, d, J=8.2 Hz), 4.67 (1 H, br s), 4.87 (1 H, d, J=4.1 Hz), 5.22–5.25 (2 H, m), 5.48 (1 H, d, J=10.8 Hz), 5.60 (1 H, d, J=17.3 Hz), 5.62–5.64 (1 H, m), 5.69 (1 H, dd, J=4.1, 10.3 Hz), 5.98–6.13 (4 H, m), 6.21 (1 H, d, J=8.3 Hz), 7.29–7.33 (1 H, m), 7.43–7.50 (3 H, m), 7.60 (1 H, t, J=7.3 Hz), 8.15 (2 H, d, J=7.6 Hz), 8.39 (1 H, d, J=4.6 Hz).

EXAMPLE 11

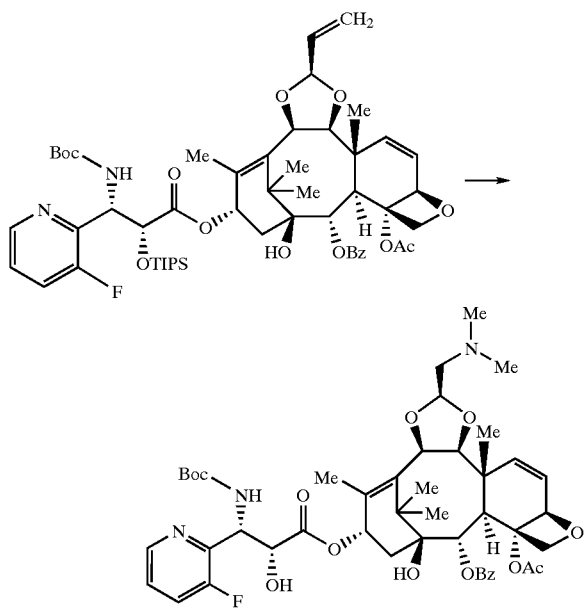

(1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-6,11-dien-13-yl (2R,3S)-3-(tert-butoxycarbonylamino)-3-(3-fluoro-2-pyridyl)-2-hydroxypropionate The title compound was obtained by carrying out the same procedure of the step 2 of Example 1, except that the compound obtained in the step 2 of Example 9 was used as the material.

¹H-NMR (400 MHz, CDCl₃, TMS) δ: 1.28 (3 H, s), 1.39 (9 H, s), 1.52 (3 H, s), 1.57 (3 H, s), 1.72 (3 H, s), 1.86 (1 H, s), 2.27–2.46 (2 H, m), 2.39 (6 H, s), 2.41 (3 H, s), 2.69 (1 H, dd, J=5.2, 13.2 Hz), 2.79 (1 H, dd, J=4.2, 13.2 Hz), 3.11 (1 H, d, J=5.9 Hz), 3.98 (1 H, d, J=7.6 Hz), 4.28 (1 H, d, J=8.1 Hz), 4.33 (1 H, d, J=8.3 Hz), 4.66 (1 H, d, J=2.5 Hz), 4.87 (1 H, d, J=4.1 Hz), 5.02 (1 H, dd, J=4.2, 4.8 Hz), 5.17 (1 H, d, J=7.8 Hz), 5.62 (1 H, d, J=8.5 Hz), 5.68 (1 H, dd, J=4.1, 10.3 Hz), 5.96 (1 H, m), 6.10 (2 H, m), 6.20 (1 H, d, J=6.9 Hz), 7.27–7.60 (6 H, m), 8.15 (2 H, d, J=7.3 Hz), 8.40 (1 H, d, J=4.6 Hz).

EXAMPLE 12

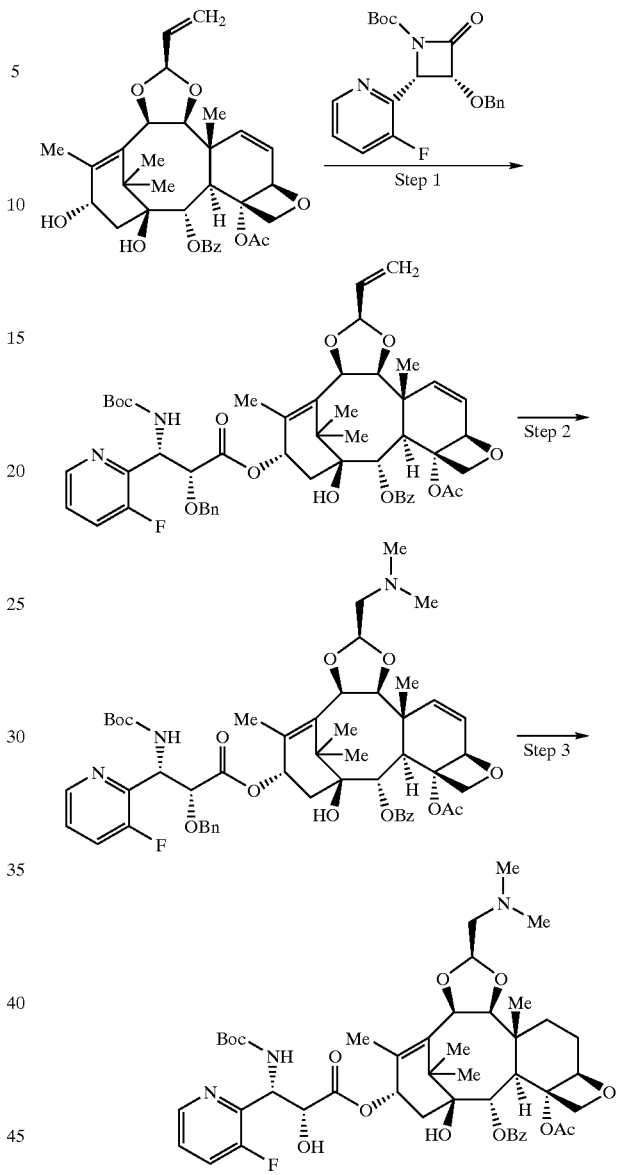

Step 1: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-6,11-dien-13-yl (2R,3S)-2-benzyloxy-3-(tert-butoxycarbonylamino)-3-(3-fluoro-2-pyridyl)propionate The title compound was obtained by carrying out the same procedure of the step 1 of Example 8, except that (3R,4S)-3-benzyloxy-1-(tert-butoxycarbonyl)-4-(3-fluoro-2-pyridyl)-2-azetidinone was used instead of (3R,4S)-1-(tert-butoxycarbonyl)-4-(5-methoxy-2-pyridyl)-3-triisopropylsilyloxy-2-azetidinone.

¹H-NMR (400 MHz, CDCl₃, TMS) δ: 1.32 (3 H, s), 1.39 (9 H, s), 1.56 (3 H, s), 1.59 (3 H, s), 1.77 (3 H, s), 1.85 (1 H, s), 2.31 (3 H, s), 2.39 (2 H, m), 3.13 (1 H, d, J=6.1 Hz), 4.07 (1 H, d, J=7.6 Hz), 4.18 (1 H, d, J=12.0 Hz), 4.31 (3 H, m), 4.68 (1 H, d, J=12.2 Hz), 4.90 (1 H, d, J=4.2 Hz), 5.23 (2 H, t, J=7.1 Hz), 5.48 (1 H, d, J=11.0 Hz), 5.59 (2 H, m), 5.70 (1 H, dd, J=4.4, 10.5 Hz), 6.02 (1 H, m), 6.13 (2 H, d, J=10.2 Hz), 6.26 (1 H, d, J=9.0 Hz), 6.88 (2 H, d, J=7.1 Hz), 7.19 (3 H, m), 7.29 (2 H, t, J=6.8 Hz), 7.49 (2 H, t, J=7.8 Hz), 7.60 (1 H, t, J=7.3 Hz), 8.16 (2 H, d, J=7.3 Hz), 8.42 (1 H, m).

Step 2: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-6,11-dien-13-yl (2R,3S)-2-benzyloxy-3-(tert-butoxycarbonylamino)-3-(3-fluoro-2-pyridyl)propionate The title compound was obtained by carrying out the same procedure of the step 2 of Example 8, except that the compound obtained in the above step 1 was used as the material, and dimethylamine (2 M methanol solution) was used instead of morpholine.

$^1$H-NMR (400 MHz, CDCl$_3$, TMS) δ: 1.26 (3 H, s), 1.39 (9 H, s), 1.54 (3 H, s), 1.57 (3 H, s), 1.75 (3 H, s), 1.82 (1 H, s), 2.31 (3 H, s), 2.36–2.39 (2 H, m), 2.38 (6 H, s), 2.71 (1 H, dd, J=5.2, 13.2 Hz), 2.77 (1 H, dd, J=4.1, 13.2 Hz), 3.12 (1 H, d, J=5.6 Hz), 4.02 (1 H, d, J=7.8 Hz), 4.19 (1 H, d, J=12.2 Hz), 4.31 (2 H, m), 4.36 (1 H, d, J=2.9 Hz), 4.68 (1 H, d, J=12.7 Hz), 4.88 (1 H, d, J=4.1 Hz), 5.01 (1 H, t, J=4.7 Hz), 5.16 (1 H, d, J=7.8 Hz), 5.60 (1 H, d, J=8.8 Hz), 5.69 (1 H, dd, J=4.2, 10.3 Hz), 5.93 (1 H, d, J=5.6 Hz), 6.11 (2 H, m), 6.23 (1 H, d, J=9.3 Hz), 6.88 (2 H, d, J=6.6 Hz), 7.16–7.31 (5 H, m), 7.48 (1 H, t, J=7.8 Hz), 7.59 (1 H, t, J=7.3 Hz), 8.15 (2 H, dd, J=1.5, 7.1 Hz), 8.41 (1 H, d, J=2.9 Hz).

Step 3: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate The title compound was obtained by carrying out the same procedure of the step 3 of Example 8, except that the compound obtained in the above step 2 was used as the material. Its instrumental analysis data coincided with those of the compound obtained in the step 3 of Example 7.

EXAMPLE 13

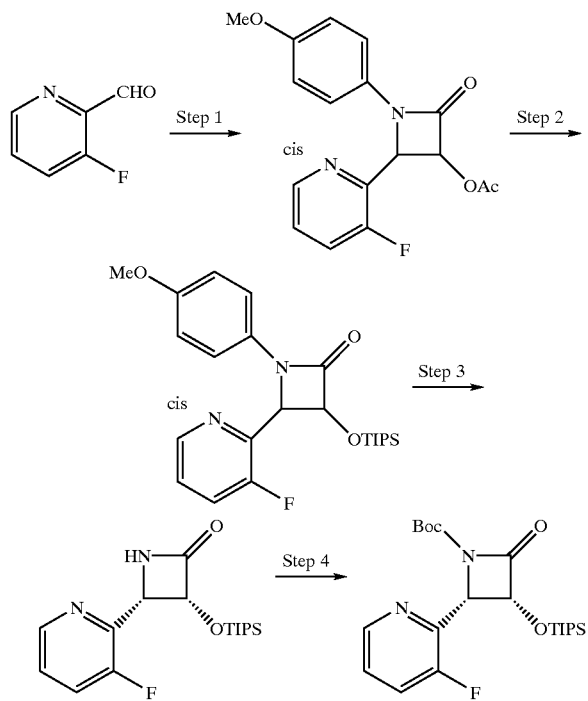

Step 1: (±)-cis-3-Acetoxy-4-(3-fluoro-2-pyridyl)-1-(4-methoxyphenyl)-2-azetidinone In 100 ml of benzene were dissolved 20 g of 3-fluoro-2-formylpyridine and 15.6 g of 4-anisidine. To the resulting solution was added 20 g of anhydrous sodium sulfate, followed by stirring at room temperature for 1 hour. The insoluble matter was filtered off and the filtrate was concentrated under reduced pressure. The residue was dissolved in 400 ml of methylene chloride, 26.5 ml of triethylamine and 20.4 ml of 2-acetoxyacetyl chloride were added thereto at −60° C., and the resulting mixture was heated to room temperature overnight. To the reaction mixture was added 300 ml of water to separate the mixture into two layers. The extract obtained by extracting the water layer with chloroform was combined with the organic layer. The mixture was washed successively with a saturated aqueous solution of sodium bicarbonate and saturated brine, and dried over anhydrous sodium sulfate. The solvent was evaporated under a reduced pressure and the resulting residue was purified by a silica gel column chromatography (eluted with ethyl acetate) to obtain 33.2 g of the title compound as a white substance.

$^1$H-NMR (400 MHz, CDCl$_3$, TMS) d: 1.80 (3H, s), 3.74 (3H, s), 5.72 (1H, d, J=5.1 Hz), 6.09 (1H, d, J=5.1 Hz), 6.78–6.82 (2H, m), 7.23–7.29 (2H, m), 7.30–7.33 (1H, m), 7.41–7.46 (1H, m), 8.44–8.46 (1H, m).

Step 2: (±)-cis-4-(3-Fluoro-2-pyridyl)-1-(4-methoxyphenyl)-3-triisopropylsilyloxy-2-azetidinone In a mixed solvent of 180 ml of tetrahydrofuran and 180 ml of methanol was dissolved 18 g of the compound obtained in the step 1. To the solution was added 500 mg of potassium carbonate, followed by stirring at room temperature for 1 hour. After neutralization of the reaction mixture with a strong acidic resin, the insoluble matter was filtered off. The filtrate was concentrated under reduced pressure. The residue was dissolved in 180 ml of dimethylformamide. Under ice cooling, 5.6 g of imidazole and 17.5 ml of triisopropylsilyl chloride were added to the resulting solution and the mixture was stirred at room temperature overnight. The reaction mixture was poured into ice water and extracted with ethyl acetate. The extract was washed successively with water and saturated brine, and dried over anhydrous sodium sulfate. The solvent was evaporated under a reduced pressure and the resulting residue was washed with hexane to obtain 20 g of the title compound as a white substance.

$^1$H-NMR (400 MHz, CDCl$_3$, TMS) d: 0.91–1.07 (21H, m), 3.74 (3H, s), 5.38 (1H, d, J=4.9 Hz), 5.50 (1H, d, J=4.9 Hz), 6.78–6.81 (2H, m), 7.23–7.28 (3H, m), 7.34–7.39 (1H, m), 8.41–8.43 (1H, m).

Step 3: (3R,4S)-4-(3-Fluoro-2-pyridyl)-3-triisopropylsilyloxy-2-azetidinone

In 50 ml of acetonitrile was dissolved 1.0 g of the compound obtained in the above-described step 2. Under ice cooling, 20 ml of an aqueous solution of 3.7 g of cerium (IV) ammonium nitrate was added to the resulting solution, followed by stirring at the same temperature for 30 minutes. To the reaction mixture were added a saturated aqueous solution of sodium bicarbonate, a saturated aqueous solution of sodium sulfite and ethyl acetate to separate the mixture into two layers. The water layer was extracted with ethyl acetate. The extract and the organic layer obtained above were combined. The mixture was washed with saturated brine, and dried over anhydrous sodium sulfate. The solvent was evaporated under a reduced pressure and the resulting residue was purified by a silica gel column chromatography (eluted with hexane:ethyl acetate=2:1 (v/v)) to obtain 0.4 g of (±)-cis-4-(3-fluoro-2-pyridyl)-3-triisopropylsilyloxy-2-azetidinone. The compound was resolved by an optically active column, whereby 0.18 g of the title compound was obtained as a white substance.

$^1$H-NMR (400 MHz, CDCl$_3$, TMS) d: 0.89–1.06 (21H, m), 5.17 (1H, dd, J=1.0, 4.9 Hz), 5.35 (1H, dd, J=1.4, 4.9 Hz), 6.24 (1H, br s), 7.23–7.28 (1H, m), 7.37 (1H, dt, J=1.5, 8.3 Hz), 8.43 (1H, d, J=4.4 Hz).

$[\alpha]_D^{23}$ +38° (c=0.11, CHCl$_3$)

Resolution Conditions:

Column: "CHIRALCEL OD" (20 mm×250 mm) produced by Daicel Chemical Industries, Ltd.

Solvent: hexane: 2-propanol=92:8 (v/v)

Flow rate: 10 min/min

Retention time: 10 minutes [(3S,4R)-form], 14 minutes [(3R,4S)-form]

Step 4: (3R,4S)-1-(tert-Butoxycarbonyl)-4-(3-fluoro-2-pyridyl)-3-triisopropylsilyloxy-2-azetidinone In 5 ml of tetrahydrofuran were dissolved 0.18 g of the compound obtained in the above-described step 3 and 0.17 g of di-tert-butyl dicarbonate. To the resulting solution was added 13 mg of 4-dimethylaminopyridine, followed by stirring at room temperature for 1 hour. Under reduced pressure, the reaction mixture was concentrated, the resulting residue was purified by a silica gel column chromatography (eluted with hexane:ethyl acetate=5:1 (v/v)) to obtain 0.24 g of the title compound as an oily substance.

$^1$H-NMR (400 MHz, CDCl$_3$, TMS) d: 0.88–1.03 (21H, m), 1.44 (9H, s), 5.27 (1H, d, J=5.8 Hz), 5.46 (1H, d, J=5.8 Hz), 7.24–7.26 (1H, m), 7.38 (1H, t, J=8.8 Hz), 8.42 (1H, d, J=3.9 Hz).

$[\alpha]_D^{18}$ +86° (c=1.03, CHCl$_3$)

EXAMPLE 14

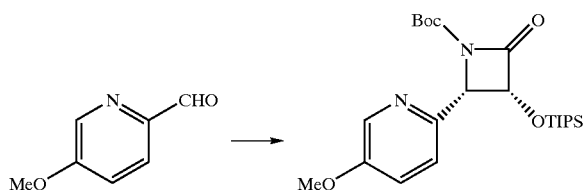

(3R,4S)-1-(tert-Butoxycarbonyl)-4-(5-methoxy-2-pyridyl)-3-triisopropylsilyloxy-2-azetidinone The title compound was obtained as an oily substance by carrying out the same procedure of the steps of Example 13, except that 5-methoxy-2-formylpyridine was used instead of 3-fluoro-2-formylpyridine.

$^1$H-NMR (400 MHz, CDCl$_3$, TMS) d: 0.88–1.01 (21H, m), 1.43 (9H, s), 3.85 (3H, s), 5.10 (1H, d, J=5.8 Hz), 5.29 (1H, d, J=5.8 Hz), 7.18–7.28 (2H, m), 8.27 (1H, d, J=3 Hz).

EXAMPLE 15

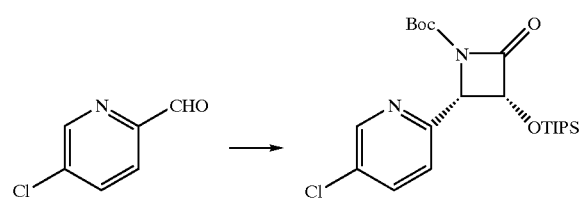

(3R,4S)-1-(tert-Butoxycarbonyl)-4-(5-chloro-2-pyridyl)-3-triisopropylsilyloxy-2-azetidinone The title compound was obtained as an oily substance in the same procedure of the steps of Example 13, except that 5-chloro-2-formylpyridine was used instead of 3-fluoro-2-formylpyridine.

$^1$H-NMR (400 MHz, CDCl$_3$, TMS) d: 0.88–1.02 (21H, m), 1.44 (9H, s), 5.12 (1H, d, J=4.9 Hz), 5.31 (1H, d, J=4.9 Hz), 7.29 (1H, d, J=8.3 Hz), 7.68 (1H, dd, J=2.4, 8.3 Hz), 8.54 (1H, d, J=2.4 Hz).

EXAMPLE 16

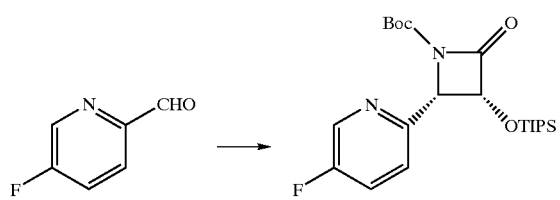

(3R,4S)-1-(tert-Butoxycarbonyl)-4-(5-fluoro-2-pyridyl)-3-triisopropylsilyloxy-2-azetidinone The title compound was obtained as an oily substance in the same procedure of the steps of Example 13, except that 5-fluoro-2-formylpyridine was used instead of 3-fluoro-2-formylpyridine.

$^1$H-NMR (400 MHz, CDCl$_3$, TMS) d: 0.88–1.01 (21H, m), 1.44 (9H, s), 5.14 (1H, d, J=4.9 Hz), 5.33 (1H, d, J=4.9 Hz), 7.33–7.45 (2H, m), 8.44 (1H, d, J=2.9 Hz).

EXAMPLE 17

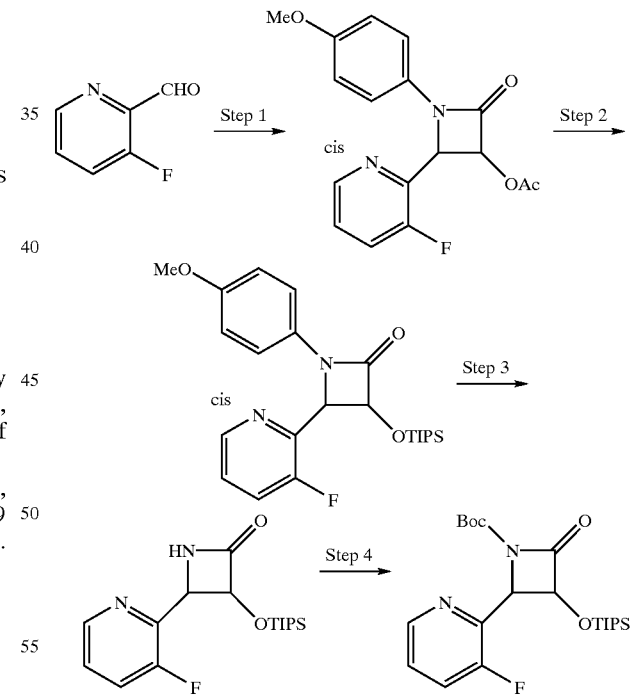

(±)-1-(tert-Butoxycarbonyl)-4-(3-fluoro-2-pyridyl)-3-triisopropylsilyloxy-2-azetidinone The racemic modification obtained in the step 3 of Example 13 without optical resolution was treated in a similar manner to the step 4, whereby the title compound was obtained. NMR data of this compound were found to coincide with those of the compound obtained in the step 4 of Example 13.

EXAMPLE 18

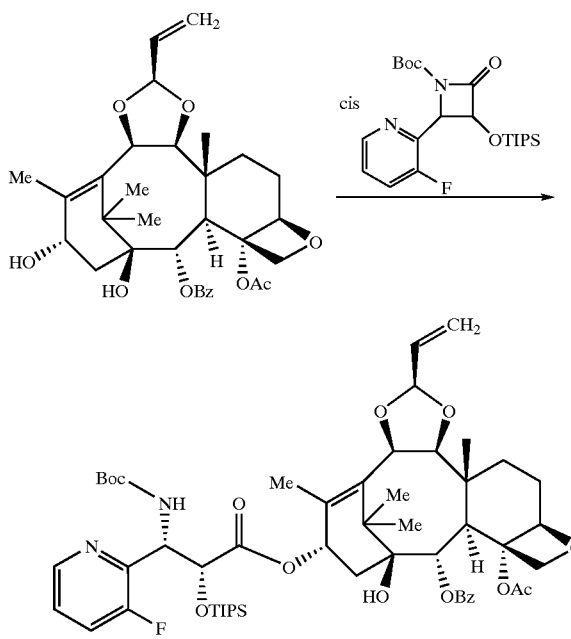

(1S,2S,3R,4S,5R,8R,9S,10R,13S)-4-acetoxy-2-benzoyloxy-5,20-epoxy-1-hydroxy-9,10-[(1S)-2-propenylidenedioxy]tax-11-en-13-yl (2R,3S)-3-(tert-butoxycarbonylamino)-3-(3-fluoro-2-pyridyl)-2-triisopropylsilyloxypropionate In 20 ml of dry tetrahydrofuran was dissolved 0.56 g of (1S,2S,3R,4S,5R,8R,9S,10R,13S)-4-acetoxy-2-benzoyloxy-5,20-epoxy-1,13-dihydroxy-9,10-[(1S)-2-propenylidenedioxy]tax-11-ene. To the resulting solution was added 1.2 ml of lithium hexamethyl disilazide (1 mole tetrahydrofuran solution) was added at −60° C., and the mixture was stirred for 20 minutes. At the same temperature, a 5 ml tetrahydrofuran solution of 1.1 g of (±)-cis-1-(tert-butoxycarbonyl)-4-(3-fluoro-2-pyridyl)-3-triisopropylsilyloxy-2-azetidinone was added to the reaction mixture, and the mixture was stirred for 20 minutes under ice cooling. A saturated aqueous solution of ammonium chloride and ethyl acetate were added to the reaction mixture to separate it into two layers. The water layer was extracted with ethyl acetate. After the extract and the organic layer obtained above were combined, the mixture was washed successively with a saturated aqueous solution of sodium bicarbonate and saturated brine, and dried over anhydrous sodium sulfate. The solvent was evaporated under reduced pressure and the resulting residue was purified by a silica gel chromatography (eluted with hexane:ethyl acetate=5:1 (v/v)) to obtain 0.9 g of the title compound as a white substance. The instrumental data were found to coincide with those of the compound obtained in the step 1 of Example 6.

EXAMPLE 19

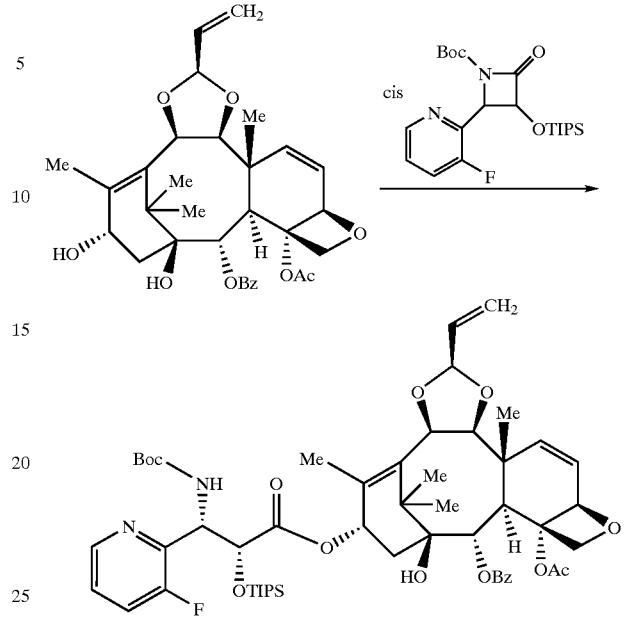

(1S,2S,3R,4S,5R,8R,9S,10R,13S)-4-Acetoxy-2-benzoyloxy-5,20-epoxy-1-hydroxy-9,10-[(1S)-2-propenylidenedioxy]tax-6,11-dien-13-yl (2R,3S)-3-(tert-butoxycarbonylamino)-3-(3-fluoro-2-pyridyl)-2-triisopropylsilyloxypropionate In 400 ml of dry tetrahydrofuran was dissolved 21 g of (1S,2S,3R,4S,5R,8R,9S,10R,13S)-4-acetoxy-2-benzoyloxy-5,20-epoxy-1,13-dihydroxy-9,10-[(1S)-2-propenylidenedioxy]tax-6-11-diene. To the resulting solution was added 44.5 ml of lithium hexamethyl disilazide (1 mole tetrahydrofuran solution) at −60° C., and the mixture was stirred for 20 minutes. At the same temperature, a 100 ml tetrahydrofuran solution of 39 g of (±)-cis-1-(tert-butoxycarbonyl)-4-(3-fluoro-2-pyridyl)-3-triisopropylsilyloxy-2-azetidinone was added to the reaction mixture, and the mixture was stirred for 20 minutes under ice cooling. A saturated aqueous solution of ammonium chloride and ethyl acetate were added to the reaction mixture to separate the mixture into two layers. The water layer was extracted with ethyl acetate. After the extract and the organic layer obtained above were combined, the mixture was washed successively with a saturated aqueous solution of sodium bicarbonate and saturated brine, and dried over anhydrous sodium sulfate. The solvent was evaporated under reduced pressure and the resulting residue was purified by a silica gel chromatography (eluted with hexane-:ethyl acetate=7:1 (v/v)) to obtain 33 g of the title compound as a white substance. The instrumental data were found to coincide with those of the compound obtained in the step 1 of Example 9.

Test Example 1

Mouse fibrosarcoma Meth A was subcutaneously transplanted into mice (line name; Balb/c), and each compound dissolved in a mixed solvent of ethanol, Tween 80 and 5% glucose (5:5:90 (v/v)) was administered by intravenous injection after 6, 8 or 10 days (or only after 6 days) of the transplantation. Each animal was anatomized on the 17th day to examine tumor weight, platelet numbers and renal toxicity. Six mice were used in each group.

Antitumor effect was calculated by the following formula.

{1−(tumor weight of compound-administered group/tumor weight of solvent-administered group)}×100

The number of platelets was expressed by (platelets of compound-administered group/platelets of solvent-administered group)×100.

The renal toxicity findings were expressed as "changed" when a change such as fading was found by macroscopic observation at the time of anatomy or when a change such as precipitation of hyaline droplet substance in the renal tubular cell cytoplasm was found by a histological inspection.

TABLE 1

| Compound | Dose (mg/kg) | Antitumor effect (%) | Platelet numbers (%) | Renal toxicity findings |
|---|---|---|---|---|
| Example 51 of JP-A-9-12578 | 1.5 × 3 | 75 | 37 | changed |
| Example 70 of JP-A-9-12578 | 0.98 × 3 | 78 | 55 | changed |
| Example 81 of JP-A-9-12578 | 2.2 × 3 | 62 | 58 | changed |
| Example 121 of JP-A-9-12578 | 0.43 × 3 | 75 | 57 | changed |
| Compound (B) | 32.4 × 1[a] | 83 | 142 | no change |
| Compound (B) | 22.5 × 1 | 69 | 124 | — |

[a] Three deaths among 6 animals used.

Test Example 2

B16 Melanoma BL6 was subcutaneously transplanted into mice (C57BL/6), and each compound was administered 4 days thereafter. In the case of intravenous administration, the compound of formula A was administered by dissolving it in a mixed solvent of ethanol, Tween 80 and 5% glucose (5:15:80 (v/v)), and the compound of Example 7 by dissolving in the same mixed solvent of 5:5:90 (v/v). In the case of oral administration, each compound was administered by suspending it in a 0.5% carboxymethylcellulose sodium aqueous solution. Each animal was anatomized after 15 days of the transplantation to measure tumor weight. Antitumor effect was calculated by the following formula.

{1−(tumor weight of compound-administered group/tumor weight of solvent-administered group)}×100

Six mice were used in each group.

TABLE 2

| Compound | Dose (mg/kg) | Rout of administration | Antitumor effect (%) |
|---|---|---|---|
| Compound (A) | 180.0 | intravenous | 95.7 |
|  | 600.0 | oral | 6.2 |
| Compound (B) | 20.0 | oral | 97.4 |
|  | 13.3 | oral | 90.5 |
| Compound of Example 7 | 11.9 | intravenous | 95.5 |
|  | 7.9 | intravenous | 91.5 |
|  | 11.9 | oral | 97.4 |
|  | 7.9 | oral | 91.5 |

Test Example 3
Metabolism in Human Microsome P450

Each of the samples to be evaluated was dissolved in acetonitrile/water (1:1, v/v) to a concentration of 500 $\mu$M, and the solution was mixed with human liver microsome (Xenotech LLC) and other components such as various coenzymes and buffer solution and allowed to generate the metabolic reaction at 37° C. The reaction solution was composed of phosphate buffer (0.076 M; final concentration, the same shall apply hereinafter), sample to be evaluated (10 $\mu$M), human liver microsome (1 mg/ml), glucose 6-phosphate (10 mM), glucose-6-phosphate dehydrogenase (1 unit/ml), magnesium chloride (4 mM) and reduced nicotinamide adenine dinucleotide phosphate ($\beta$-NADPH, 1 mM), and 500 $\mu$l of the solution was used in one reaction. In this case, the reaction solution excluding $\beta$-NADPH was incubated in advance at 37° C. for 2 minutes and then the reaction was started by adding a $\beta$-NADPH aqueous solution (50 mM, 10 $\mu$l).

The reaction was terminated by adding 1 ml of ice-cooled acetonitrile 1, 2 or 5 minutes after commencement of the reaction.

In this connection, a sample of 0 minute after commencement of the reaction was prepared by adding water instead of the $\beta$-NADPH aqueous solution and immediately adding 1 ml of acetonitrile. A 100 $\mu$l portion of an internal standard substance was added to each of these samples, and the reaction solution was centrifuged for 15 minutes. The resulting supernatant was injected into a high performance liquid chromatography (HPLC) to measure concentration of the sample to be evaluated. The amount decreased from the concentration at 0 minute of the commencement of reaction was used as the formed amount of the metabolite (nmol/mg protein). By plotting the amount of formed metabolite against the reaction time and carrying out linear regression by the method of least squares, amount of the metabolite formed per 1 minute (metabolic rate constant: k (nmol/min/mg protein)) was calculated from the slope.

From the thus obtained metabolic rate constant k (nmol/min/mg protein), the liver-specific clearance (CLint) was calculated by the following formula.

CLint (ml/min/kg body weight)=$k$×($g$ liver weight)/(kg body weight)×(45 mg of microsome protein)/($g$ liver weight), wherein the liver weight per 1 kg body weight is 20 g.

Also, the liver clearance (CLh) was calculated from the CLint in accordance with the Well-stirred model (*J. Pharmacol. Exp. Ther.*, 283, 46–58, 1997).

CLh (ml/min/kg body weight)=$Q$×CLint/($Q$+CLint), wherein Q is the liver blood flow in human defined to be 20 ml/min/kg.

Theoretical bioavailability (F) value was calculated from the CLh by the following formula.

F=(1−CLh/Q)

In addition, theoretical bioavailability value of unchanged compound was calculated by a formula 1−F.

TABLE 3

|  | Compound (B) | Ex. 1 | Ex. 3 | Ex. 7 |
|---|---|---|---|---|
| Metabolic rate constant (nmol/min/mg protein) | 0.59 | 0.15 | 0.02 | 0.08 |
| Clint (ml/min/kg) | 53.1 | 13.5 | 1.8 | 7.2 |
| Theoretical F value of unchanged compound | 0.27 | 0.60 | 0.92 | 0.74 |

The results are shown in FIG. 1 and Table 1. Theoretical F values of the unchanged form of compounds of the invention were larger that the theoretical F value 0.27 of the unchanged form of the control compound (compound of formula B), meaning that the variability range of bioavailability is suppressed, separation of the therapeutic range and toxicity range can be effected more accurately and the oral administration can therefore be made.

Test Example 4

The compound of formula (B) or of Example 7 was intravenously or orally administered to a monkey by single dose, and changes in its blood concentration was measured to calculate $AUC0_{0-\infty}$. The $AUC0_{0-\infty}$ means area under the blood concentration time curve of a drug concentration in blood during a period of from the time of administration (0 h) to the infinite time and it can be calculated in accordance with the method (trapezoidal rule) disclosed in Kiyoshi Yamaoka and Yusuke Tanigawara, Yakubutsu Sokudoron Nyumon (A Guide to Pharmacokinetics), pages 116–117. In addition, ratio of the AUC at the time of oral administration to the AUC at the time of intravenous administration was calculated as oral BA. Test of the compound of formula (B) was carried out using different individual of one monkey for the intravenous and oral administration, and test of the compound of Example 7 was carried out using the same individuals of 4 monkeys for the intravenous and oral administration to calculate average AUC value.

Animal: female *Macaca irus*, Administration method (compound of formula (B)) [intravenous] EtOH:Tween 80:5% glucose=5:5:90, [oral] 0.1 N HCl solution, (compound of Example 7) [intravenous] 10% β-CyD-SBE7 (pH=3.5 in physiological saline), [oral] 40 mM acetate buffer (pH 4.0)

TABLE 4

| | Dose (mg/kg) | $AUC_{0-\infty}$ (ng · h/ml) | | Oral BA (%) |
| --- | --- | --- | --- | --- |
| | | Intravenous | Oral | |
| Compound (B) | 1.6 | 394.1 | 28.1 | 7.1 |
| Compound of Example 7 | 1.8 | 993.8 | 620.6 | 62.4 |

Industrial Applicability

The compound of the invention was improved in terms of its toxicity and showed no renal toxicity. The compound of the invention showed high antitumor effect by its oral administration to mice. Since the compound of the invention has a large theoretical F value of its unchanged form, the variability range of bioavailability is suppressed and separation of the therapeutic range and toxicity range can be effected. The compound of the invention showed excellent oral absorption property in monkey. Accordingly, the compound of the invention can be used as an antitumor agent which can be orally administered.

What is claimed is:
1. A compound represented by formula (I):

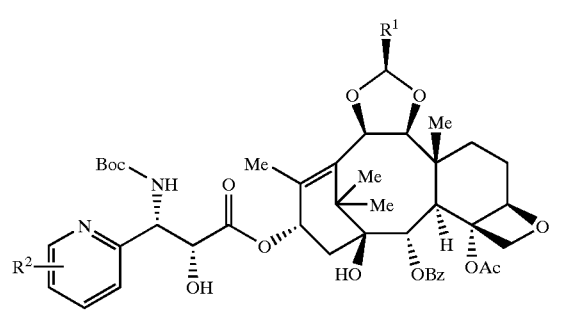

wherein $R^1$ represents a dimethylaminomethyl group or a morpholinomethyl group and $R^2$ represents a halogen atom or an alkoxy group having from 1 to 6 carbon atoms, or a salt thereof.

2. The compound or a salt thereof according to claim 1, wherein $R^2$ is a methoxy group or a fluorine atom.

3. A compound represented by formula (II):

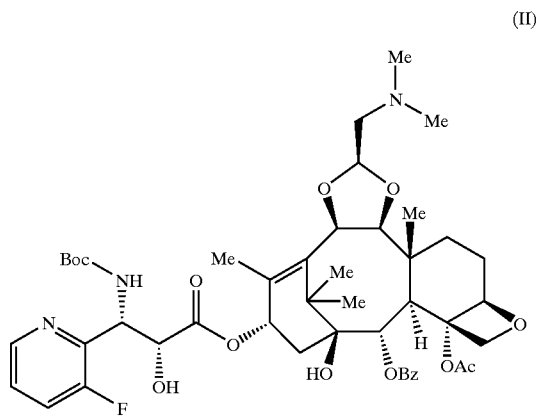

or a salt thereof.

4. A medicament which comprises a compound or a salt thereof described in any one of claims 1 to 3.

5. An antitumor agent which contains a compound or a salt thereof described in any one of claims 1 to 3.

6. A compound represented by formula (III):

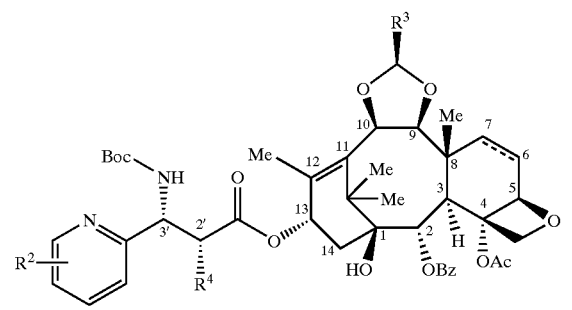

wherein $R^3$ represents a dimethylaminomethyl group, a morpholinomethyl group or a vinyl group, $R^4$ represents a hydroxyl group which may have a protecting group and $R^2$ represents a halogen atom or an alkoxy group having from 1 to 6 carbon atoms, and wherein the bond represented by the dotted line between the 6-position and 7-position of a partial structure shown by formula:

may become a double bond, or a salt thereof.

7. A compound represented by formula (IV):

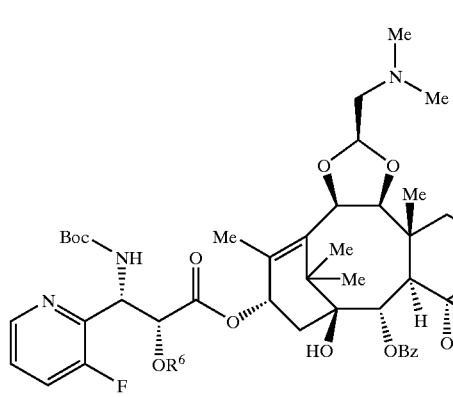

wherein $R^6$ represents a triisopropylsilyl group, a tertiary butyldimethylsilyl group, a triethylsilyl group or a benzyl group, or a salt thereof.

8. A compound represented by formula (V):

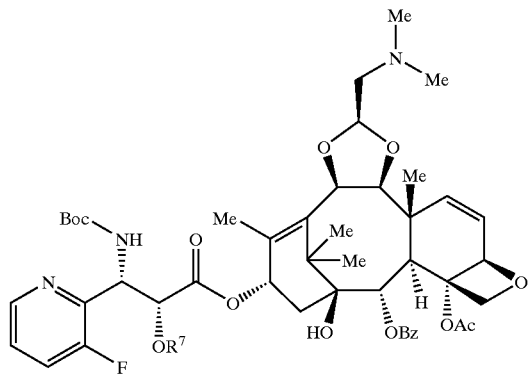

wherein $R^7$ represents a triisopropylsilyl group, a tertiary butyldimethylsilyl group, a triethylsilyl group or a benzyl group, or a salt thereof.

9. A compound represented by formula (VI):

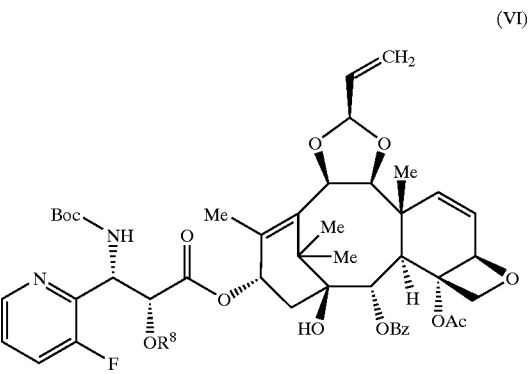

wherein $R^8$ represents a triisopropylsilyl group, a tertiary butyldimethylsilyl group, a triethylsilyl group or a benzyl group, or a salt thereof.

10. A process for preparing a compound represented by formula (I):

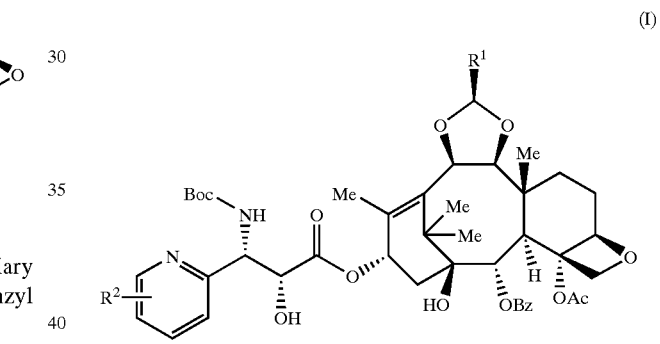

wherein $R^1$ represents a dimethylaminomethyl group or a morpholinomethyl group and $R^2$ represents a halogen atom or an alkoxy group having from 1 to 6 carbon atoms, which comprises the following steps 1), 2), 3), 4) and 5):

1) reacting a compound represented by (III'):

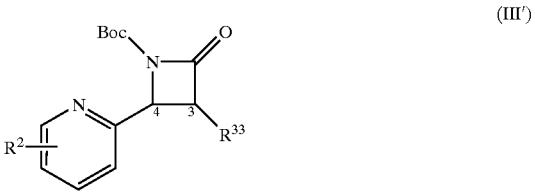

wherein $R^2$ represents a halogen atom or an alkoxy group having 1 to 6 carbon atoms, and $R^{33}$ represents a hydroxyl group optionally having a protecting group, in which $R^{33}$ at the 3-position on the β-lactam ring is in a cis configuration relative to the pyridyl group at the 4-position, with a compound represented by formula (IV'):

(IV')

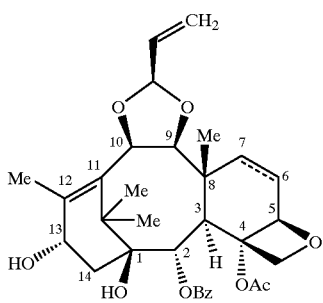

wherein the bond represented by the dotted line between the 6-position and 7-position of a partial structure shown by formula (V'):

(V')

may became a double bond, thereby obtaining a compound represented by formula (VI'):

(VI')

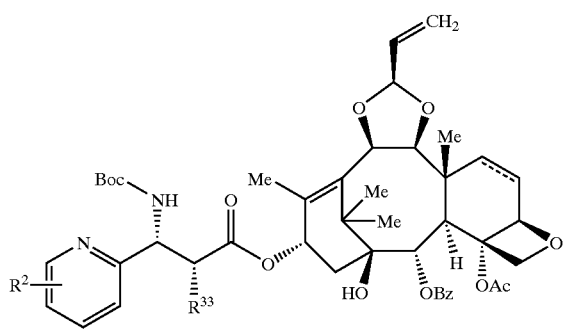

2) converting the vinyl group of the resulting compound into an aldehyde group,
3) converting the aldehyde group into a dimethylaminomethyl or a morpholinomethyl group,
4) when the bond between the 6-carbon atom and 7-carbon atom is a double bond, converting the bond into a single bond, and
5) when $R^{33}$ is a hydroxyl group having a protecting group, removing said protecting group.

11. A process according to claim 10, wherein the compound represented by formula (III'):

(III')

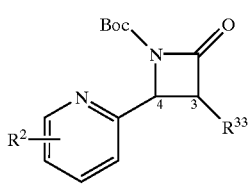

wherein, $R^2$ represents a halogen atom or an alkoxy group having 1 to 6 carbon atoms, and $R^{33}$ represents a hydroxyl group optionally having a protecting group, in which $R^{33}$ at the 3-position on the β-lactam ring is in a cis configuration relative to the pyridyl group at the 4-position, is an optically active compound and is a compound represented by formula (VII'):

(VII')

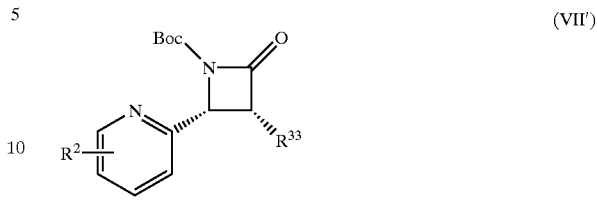

wherein, $R^2$ represents a halogen atom or an alkoxy group having 1 to 6 carbon atoms and $R^{33}$ represents a hydroxyl group optionally having a protecting group.

12. A process according to claim 10, wherein the compound represented by formula (III'):

(III')

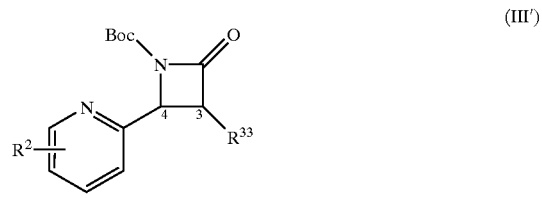

wherein $R^2$ represents a halogen atom or an alkoxy group having 1 to 6 carbon atoms and $R^{33}$ represents a hydroxyl group optionally having a protecting group, in which $R^{33}$ at the 3-position on the β-lactam ring is in a cis configuration relative to the pyridyl group at the 4-position, is a racemic compound.

13. A process according to any one of claims 10 to 12, wherein the bond between the 6-position and 7-position of a partial structure shown by formula (V') in the compound represented by formula (IV'):

(IV')

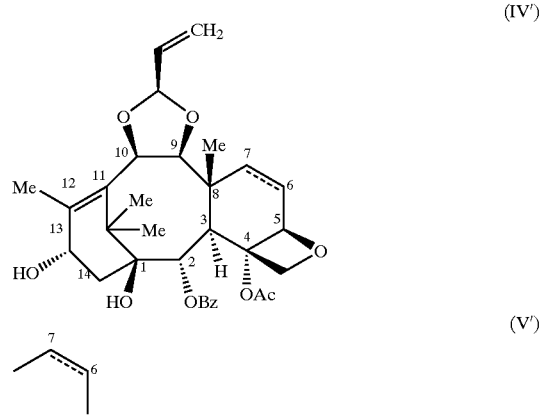

(V')

is a single bond.

14. A process according to any one of claims 10 to 12, wherein the bond between the 6-carbon atom and 7-carbon atom of the partial structure shown by the following formula (V') in the compound represented by formula (IV'):

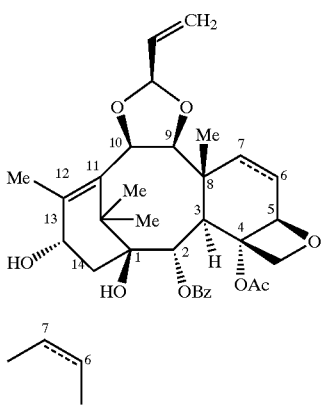

(IV')

(V')

is a double bond.

15. A process according to any one of claims 10 to 12, wherein $R^2$ represents a methoxy group or a fluorine atom.

16. A process for preparing a compound or a salt thereof according to any one of claims 1 to 3 by performing one or more of the following conversion reactions in an optional order to the compound according to claim 6:
   a. when $R^3$ is a vinyl group, first converting $R^3$ to a diol, thereafter to an adlehyde and finally converting to dimethylaminomethyl group or morpholinomethyl group by reacting with a corresponding amine,
   b. when the bond between the 6- and 7-positions is a double bond, adding hydrogen to convert the double bond to a single bond,
   c. when $R^4$ is a hydroxy group having a protecting group, removing the protective group to convert it to a hydroxyl group.

17. A process for preparing a compound or a salt thereof according to claim 3 by converting $R^6$ of the compound according to claim 7 to a hydrogen atom.

18. A process for preparing a compound or a salt thereof according to claim 3 by performing the following two conversion reactions in an optional order to the compound according to claim 8:
   a. converting the double bond between the 6- and 7-positions to a single bond by adding hydrogen to the double bond, and
   b. converting a protecting group $R^7$ of a hydroxyl group to a hydrogen atom.

19. A process for preparing a compound or a salt thereof described in claim 3 by performing the following three conversion reactions in an optional order to the compound according to claim 9:
   a. converting the terminal vinyl group to a diol, therafter to an aldehyde and finally converting to a dimethylaminomethyl group by reaction with dimethyl amine,
   b. converting the double bond between the 6 and 7 position to a single bond by adding hydrogen,
   c. converting the protecting group $R^8$ of a hydroxyl group to a hydrogen atom.

20. A method for the treatment of cancer selected from the group consisting of lung cancer, gastrointestinal cancer, ovarian cancer, uterine cancer, breast cancer, cancer of the liver, cancer of the head and neck, blood cancer, renal cancer and testicular cancer, comprising administering an effective amount of a compound according to any one of claims 1–3 to a subject in need thereof.

* * * * *